US009725732B2

(12) United States Patent
Winzer et al.

(10) Patent No.: US 9,725,732 B2
(45) Date of Patent: Aug. 8, 2017

(54) PLANT CYTOCHROME P450

(71) Applicant: Sun Pharmaceutical Industries (Australia) Pty Ltd, Notting Hill (AU)

(72) Inventors: Thilo Winzer, York (GB); Tracy Carol Walker, Latrobe (AU); Ian Alexander Graham, York (GB)

(73) Assignee: Sun Pharmaceutical Industries (Australia) Pty Ltd, Notting Hill (AU)

( * ) Notice: Subject to any disclaimer, the term of this patent is extended or adjusted under 35 U.S.C. 154(b) by 17 days.

(21) Appl. No.: 14/884,448

(22) Filed: Oct. 15, 2015

(65) Prior Publication Data

US 2016/0032305 A1 Feb. 4, 2016

Related U.S. Application Data

(62) Division of application No. 13/806,608, filed as application No. PCT/GB2011/051340 on Jul. 18, 2011, now Pat. No. 9,200,261.

(30) Foreign Application Priority Data

Jul. 22, 2010 (GB) ................................... 1012262.0
Dec. 22, 2010 (GB) ................................... 1021707.3

(51) Int. Cl.

*C12N 9/02* (2006.01)
*C12N 15/82* (2006.01)
*C12N 9/00* (2006.01)
*C07K 14/415* (2006.01)
*C12P 17/18* (2006.01)

(52) U.S. Cl.

CPC ........ *C12N 15/8243* (2013.01); *C07K 14/415* (2013.01); *C12N 9/0071* (2013.01); *C12N 9/0077* (2013.01); *C12P 17/188* (2013.01); *C12Y 114/00* (2013.01)

(58) Field of Classification Search

None

See application file for complete search history.

(56) References Cited

U.S. PATENT DOCUMENTS

| | | | |
|---|---|---|---|
| 7,390,642 | B2 | 6/2008 | Kutchan et al. |
| 9,200,261 | B2 | 12/2015 | Winzer et al. |
| 9,447,444 | B2 | 9/2016 | Winzer et al. |
| 9,458,481 | B2 | 10/2016 | Winzer et al. |
| 2005/0106588 | A1 | 5/2005 | Kutchan et al. |
| 2007/0199090 | A1 | 8/2007 | Apuya et al. |
| 2008/0196123 | A1 | 8/2008 | Kutchan et al. |
| 2009/0227796 | A1 | 9/2009 | Fist |
| 2010/0075385 | A1 | 3/2010 | Kutchan et al. |
| 2010/0184166 | A1 | 7/2010 | Sato et al. |
| 2013/0104258 | A1 | 4/2013 | Winzer et al. |
| 2013/0133105 | A1 | 5/2013 | Winzer et al. |
| 2015/0004659 | A1 | 1/2015 | Winzer et al. |
| 2016/0281121 | A1 | 9/2016 | Winzer et al. |

FOREIGN PATENT DOCUMENTS

| | | | |
|---|---|---|---|
| EP | 1 270 727 | A1 | 1/2003 |
| EP | 1 512 748 | A1 | 3/2005 |
| EP | 1 632 565 | A1 | 3/2006 |
| EP | 1 837 396 | A1 | 9/2007 |
| WO | WO 99/14351 | A1 | 3/1999 |
| WO | WO 02/101052 | A2 | 12/2002 |
| WO | WO 2006/081029 | A2 | 8/2006 |
| WO | WO 2006/138012 | A1 | 12/2006 |
| WO | WO 2008/069878 | A2 | 6/2008 |
| WO | WO 2009/005647 | A2 | 1/2009 |
| WO | WO 2009/064771 | A2 | 5/2009 |
| WO | WO 2011/161431 | A2 | 12/2011 |
| WO | WO 2012/010872 | A2 | 1/2012 |
| WO | WO 2013/136057 | A2 | 9/2013 |

OTHER PUBLICATIONS

Accession No. JQ659006 & JQ659012 & JQ659010, Jul. 17, 2012.
Accession No. JQ659007 & JQ659012 & JQ659010, Jul. 17, 2012.
Accession No. JQ659008 & JQ659011 & JQ659012 & JQ659005, Jul. 17, 2012.
Sequence alignment: Amino acid sequence alignment between GenBank Accession No. AK320249.1 and methyltransferase PSMT2 sequence of SEQ ID No: 8 in U.S. Appl. No. 13/806,310 (obtained Oct. 10, 2014).
Sequence alignment: Amino acid sequence alignment between GenBank Accession No. BT096188.1 and methyltransferase PSMT2 sequence of SEQ ID No: 8 in U.S. Appl. No. 13/806,310 (obtained Oct. 10, 2014).
Sequence alignment: Amino acid sequence alignment between GenBank Accession No. EU882980.1 and methyltransferase PSMT2 sequence of SEQ ID No: 8 in U.S. Appl. No. 13/806,310 (obtained Oct. 10, 2014).
Sequence alignment: Nucleic acid sequence alignment between GenBank Accession No. AK320249.1 and methyltransferase PSMT2 sequence of SEQ ID No: 2 in U.S. Appl. No. 13/806,310, Provided by New Zealand Intellectual Property Office on Sep. 15, 2014.
Sequence alignment: Nucleic acid sequence alignment between GenBank Accession No. BT096188.1 and methyltransferase PSMT2 sequence of SEQ ID No: 2 in U.S. Appl. No. 13/806,310, Provided by New Zealand Intellectual Property Office on Sep. 15, 2014.
Sequence alignment: Nucleic acid sequence alignment between GenBank Accession No. EU882980.1 and methyltransferase PSMT2 sequence of SEQ ID No: 2 in U.S. Appl. No. 13/806,310, Provided by New Zealand Intellectual Property Office on Sep. 15, 2014.
Accession No. AB126256, May 10, 2005.
Accession No. AB126257, May 10, 2005.
Accession No. AB374409, Jan. 10, 2008.
Accession No. A9ZT62, Feb. 26, 2008.
Accession No. D3JXF8, Mar. 23, 2010.
Accession No. GU325750, Jan. 28, 2010.
Allen et al., "Metabolic Engineering of Morphinan Alkaloids by Over-Expression and RNAi Suppression of Salutaridinol 7-O-acetyltransferase in Opium Poppy," *Plant Biotech J.* 6:22-30, 2008.

(Continued)

*Primary Examiner* — Amjad Abraham
*Assistant Examiner* — Bratislav Stankovic
(74) *Attorney, Agent, or Firm* — Klarquist Sparkman, LLP

(57) ABSTRACT

This disclosure relates to the isolation and sequencing of nucleic acid molecules that encode cytochrome P450 polypeptides from a *Papaver somniferum* cultivar; uses in the production of noscapine and identification of poppy cultivars that include genes that comprise said nucleic acid molecules.

29 Claims, 15 Drawing Sheets

(56) References Cited

OTHER PUBLICATIONS

Amino acid sequence alignment between GenBank Accession No. AK320249.1 and methyltransferase PSMT2 sequence of the current application (SEQ ID No: 8).
Amino acid sequence alignment between GenBank Accession No. BT096188.1 and methyltransferase PSMT2 sequence of the current application (SEQ ID No: 8).
Amino acid sequence alignment between GenBank Accession No. EU882980.1 and methyltransferase PSMT2 sequence of the current application (SEQ ID No: 8).
Chan et al., "Draft Genome Sequence of the Oilseed Species *Ricinus communis*," *Nat Biotechnol.* 28:951-959, 2010.
Chávez et al., "Characterization of Two Methylenedioxy Bridge-Forming Cytochrome P450-Dependent Enzymes of Alkaloid Formation in the Mexican Prickly Poppy *Argemone mexica*," *Arch. Biochem. Biophys.* 507:186-193, 2011.
Chu et al., "From Hormones to Secondary Metabolism: The Emergence of Metabolic Gene Clusters in Plants," *Plant J.* 66:66-79, 2011.
Database UniProt [Online] Accession No. Q0ZPV6, Aug. 22, 2006.
Database UniProt [Online] Accession No. B9SK36, Mar. 24, 2009.
Decker et al., "Characterization of Proteins in Latex of the Opium Poppy (*Papaver somniferum*) Using Two-Dimensional Gel Electrophoresis and Microsequencing," *Electrophoresis* 21:3500-3516, 2000.
Desgagné-Penix et al., "Integration of Deep Transcriptome and Proteome Analyses Reveals the Components of Alkaloid Metabolism in Opium Poppy Cell Cultures," *BMC Plant Biol.* 10:252, 2010.
Evertsz et al., "Research Report Hybridization Cross-Reactivity within Homologous Gene Families on Glass cDNA Microarrays," *Biotechniques* 31:1182-1192, 2001.
Facchini et al., "Developmental and Inducible Accumulation of Gene Transcripts Involved in Alkaloid Biosynthesis in Opium Poppy," *Phytochemistry* 64:177-186.
Facchini et al., "Opium Poppy: Blueprint for an Alkaloid Factory," *Phytochem Rev.* 6:97-124, 2007.
Facchini and De Luca, "Opium Poppy and Madagascar Periwinkle: Model Non-Model Systems to Investigate Alkaloid Biosynthesis in Plants," *Plant J.* 54:763-784, 2008.
Field et al., "Formation of Plant Metabolic Gene Clusters Within Dynamic Chromosomal Regions," *Proc Natl Acad Sci.* 108:16116-16121, 2011.
Frick et al., "Metabolic Engineering with a Morphine Biosynthetic P450 in Opium Poppy Surpasses Breeding," *Metab. Eng.* 9:169-176, 2007.
GenBank Accession No. AK320249.1, published May 1, 2010.
GenBank Accession No. BT096188.1, published Aug. 6, 2009.
GenBank Accession No. CAG34222.1, Jun. 14, 2004.
GenBank Accession No. EU882980.1, published Nov. 13, 2009.
Gesell et al., "CYP719B1 is Salutaridine Synthase, the C-C Phenol-Coupling Enzyme of Morphine Biosynthesis in Opium Poppy," *J. Biol. Chem.* 284:24432-24442, 2009.
Great Britain Search Report dated Oct. 15, 2010 for Great Britain Application No. GB1010471.9.
Great Britain Search Report dated Nov. 23, 2010 for Great Britain Application No. GB1012262.0.
Great Britain Search Report dated Jul. 2, 2012 for Great Britain Application No. GB1204407.9 (PSMT1).
Great Britain Search Report dated Oct. 1, 2012 for Great Britain Application No. GB1204407.9 (CYP82Y1).
Great Britain Search Report dated Oct. 1, 2012 for Great Britain Application No. GB1204407.9 (PSSDR1).
Great Britain Search Report dated Oct. 31, 2012 for Great Britain Application No. GB1204407.9 (PSATI).
Great Britain Search Report dated Oct. 31, 2012 for Great Britain Application No. GB1204407.9 (PSCXE1).
Gümüşçü et al., "Evaluation of Selected Poppy (*Papaver somniferum* L.) Lines by Their Morphine and Other Alkaloids Contents," *Eur Food Res Technol.* 226:1213-1220, 2008.
Hagel et al., "Quantitative $^1$H Nuclear Magnetic Resonance Metabolite Profiling as a Functional Genomics Platform to Investigate Alkaloid Biosynthesis in Opium Poppy," *Plant Physiol.* 147:1805-1821, 2008.
Hileman et al., "Virus-Induced Gene Silencing is an Effective Tool for Assaying Gene Function in the Basal Eudicot Species *Papaver somniferum* (Opium Poppy),"*Plant J.* 44:334-341, 2005.
Ikezawa et al., "Molecular Cloning and Characterization of Methylenedioxy Bridge-Forming Enzymes Involved in Stylopine Biosynthesis in *Eschscholzia californica*,"*FEBS J.* 274:1019-1035, 2007.
International Search Report and Written Opinion of the International Searching Authority for corresponding PCT Application No. PCT/GB2011/051340, dated Feb. 8, 2012.
Kleber da Rocha et al., "Effect of Different Culture Medium Components on Production of Alkaloid in Callus Tissues of *Cereus peruvianus* (Cactaceae)," *Acta Scientiarum Biol.* Sci. 27:37-41, 2005.
Liscombe and Facchini, "Molecular Cloning and Characterization of Tetrahydroprotoberberine cis-N-Methyltransferase, an Enzyme Involved in Alkaloid Biosynthesis in Opium Poppy," *J. Biol. Chem.* 282:14741-14751, 2007.
Morishige et al., "Molecular Characterization of the S-adenosyl-L-methionine:3'-Hydroxy-N-methylcoclaurine 4'-O-Methyltransferase Involved in Isoquinoline Alkaloid Biosynthesis in *Coptis japonica*," *J. Biol. Chem.* 275:23398-23405, 2000.
NCBI accession number: XP_002284806 dated Mar. 20, 2009.
NCBI accession number: XP_002284810.2 dated Mar. 20, 2009.
NCBI accession number: XP_002284031.1 dated Mar. 20, 2009.
New Zealand Patent Office, Further Examination Report, dated Sep. 15, 2014 (2 pages).
New Zealand Intellectual Property Office, Further Examination Report for NZ Application 604057, dated Oct. 17, 2014 (2 pages).
Nucleic acid sequence alignment between GenBank Accession No. AK320249.1 and methyltransferase PSMT2 sequence of the current application (SEQ ID No: 2).
Nucleic acid sequence alignment between GenBank Accession No. BT096188.1 and methyltransferase PSMT2 sequence of the current application (SEQ ID No: 2).
Nucleic acid sequence alignment between GenBank Accession No. EU882980.1 and methyltransferase PSMT2 sequence of the current application (SEQ ID No: 2).
Okada, "The Biosynthesis of Isoprenoids and the Mechanisms Regulating it in Plants," *Biosci Biotechol Biochem.* 75:1219-1225, 2011.
Omura and Sato, "The Carbon Monoxide-binding Pigment of Liver Microsomes" *J. Biol. Chem.* 239:2370-2378, 1964.
Ounaroon et al., "(R,S)-Reticuline 7-O-methyltransferase and (R,S)-norcoclaurine 6-O-methyltransferase of *Papaver somniferum*—cDNA Cloning and Characterization of Methyl Transfer Enzymes of Alkaloid Biosynthesis in Opium Poppy," *Plant J.* 36:808-819, 2003.
Pienkny et al., "Functional characterization of a novel benzylisoquinoline O-methyltransferase suggests its involvement in papaverine biosynthesis in opium poppy (*Papaver somniferum* L)" *The Plant Journal* 60:56-67, 2009.
Sato et al., "S-Adenosyl-L-Methionine: Scoulerine-9-O-Methyltransferase from Cultured *Coptis japonica* Cells" *Phytochem.* 32:659-664, 1993.
Schuler and Werck-Reichart, "Functional Genomics of P450s"*Annu. Rev. Plant Biol.* 54:629-667, 2003.
Sequence alignment showing alignment of SEQ ID No: 10 (Fig. 4C, PSCYP3) of the present application with NCBI accession number: XP_002284806, NCBI accession number: XP_002284810.2, and NCBI accession number: XP_002284031.1.
Takos et al., "Genomic Clustering of Cyanogenic Glucoside Biosynthetic Genes Aids Their Identification in *Lotus japonicus* and Suggests the Repeated Evolution of this Chemical Defence Pathway," *Plant J.* 68:273-286, 2011.

(56) References Cited

OTHER PUBLICATIONS

Till et al., "Mismatch Cleavage by Single-Strand Specific Nucleases," *Nucleic Acids Res.* 32:2632-2641, 2004.
Wesley et al., "Construct Design for Efficient, Effective and High-Throughput Gene Silencing in Plants," *Plant J.* 27:581-590, 2001.
Wijekoon and Facchini, "Systematic Knockdown of Morphine Pathway Enzymes in Opium Poppy Using Virus-Induced Genen Silencing," *Plant J.* 69:1052-1063, 2012.
Winzer et al., "A *Papaver somniferum* 10-Gene Cluster for Synthesis of the Anticancer Alkaloid Noscapine," *Science* 336:1704-1708, 2012.
Ziegler et al., "Comparative Macroarray Analysis of Morphine Containing *Papaver somniferum* and Eight Morphine Free *Papaver* Species Identifies an O-methyltransferase Involved in Benzylisoquinoline Biosynthesis," *Planta* 222:458-471, 2005.
Ziegler et al., "Comparative Transcript and Alkaloid Profiling in *Papaver* Species Identifies a Short Chain Dehydrogenase/Reductase Involved in Morphine Biosynthesis," *Plant J.* 48:177-192, 2006.
Ziegler et al., "Evolution of Morphine Biosynthesis in Opium Poppy," *Phytochem.* 70:1696-1707, 2009.
Ziegler et al., "Comparative transcript and alkaloid profiling in *Papaver* species identifies a short chain dehydrogenase/reductase involved in morphine biosynthesis" *The Plant Journal* 48:177-192, 2006.

Figure1a

ATGGAGTTATTCATAAAGTTACCATTTATCCAACCAATTCCTTTCAGTATTATTCTTGTTACTACAGT
TTCGATTGTTCTATTATACAGTGTCTTCTTCTGGGTTACTGATAAGAAAAAGAAGAGGAAGAAAGCAC
CAAATGCTGCAGGGGCATGGCCGTTAATAGGTCATCTCCGTCTATTGATGAACGACAAGGAACCGTTG
TATAGAGCACTAGGGAGCATGGCTGATAAGTACGGACCTGCATTCAACATCCGATTAGGTAACCAAGA
AGTTCTTGTTGTGAGTAACTGGGAGATGGTAAAACAGTGTTTTGGTAATCAAAATGATAAGCTATTTT
CGAATCGTCAAACTACATTAGCTGCAAAATACATGCTTAATCAAACAACTTCTAGCGGATTCGCACCA
TATGGACCATATTGGAGAGAGCTACGAAAGATAATGGTGCAGCAATTACTCTCTAAACAATCTTTAGA
ATCGTGGAAACATCTGAAAATCAAAGAGATGGATGCTTCATTTAGTAAACTTAACGAGTTATGCAACA
ACAACGGTACTGGAACAGCTACCCTAATTAGGATGGACGAATGGTTTGCTGAGTTGACGTTCAACGTG
ATCGCAAGAAATGTCTTTGGCTACCAAAGTGGCGGAAGGTCGACAGCGCTTACGAACGGAGATACGGA
ATCAAAGGGCGAGAGGTACAAGAAAACATTGGAAGAAGCACTTCATCTTATGTCAATTTTTGCAGTTT
CAGACATATTTCCAAGTCTAGAGTGGGTAGATCGGTTAAGAGGCCTTATAAGGAATATGAAACGCTTT
GGAGATGAGCTAAATTCAATTGCAGGGTGTCTTATTGAAGAGCACCGCCAAAAGAGATTACAATCCGT
ATCTAAAAGTGATAAAGGAGTTGGTGATGAACAAGACTTCGTTGATGTTCTCTTATCGGTTGCTGAAA
AATCGCAACTTCCTGGAGATGACCCTGATTTGGTCATCAAGTCTATGATTCTGGAAATCGTATCAGGT
GGGAGTGAGACCACATCGTCAACCTTAACTTGGGCCCTCTGTCTGTTACTGAACCATCCGCATGTGTT
AAAGAAGGCAAAAGAGGAATTAGATACGCACGTAGGAAAAGATAGGCATGTAGAAGAGTCAGATACCC
CTAAGCTCGTGTACATTAATGCAATTATCAAAGAATCAATGCGATTGTATCCAAACGGGGCAATGCTT
GATCGGTTGGCGTTAGAAGAGTGCGAAGTTGGTGGATTTCATGTACCGGCCGGGGGACGCTTATTTGT
CAATGTTTGGAAGATTCAGAGAGATCCGAGTGTTTGGGAGAATCCTCTGGAGTTTAAACCAGAGAGGT
GGTTTTTGAGTAATGGTGAAAAGATGGATGTGGATTACAAAGGTCACAATCATGAATTCATACCATTT
GGGATAGGTCGGAGGATGTGCGCTGGTATGCTTTGGGCATCGGAGGTGATTCATTTGGTGCTGCCCCG
TCTTATTCATGGGTTTGATATGAAAGCAGCAAGTGCCAATGGGAAAGTAGATATGGCAGAAATGGCAG
GCATGGTGATTTGTTTTAAGAAGACACCTCTTGAAGTTATGGTCAATCCTCGAGAGTAG

Figure 1b

ATGATCATGAGTAACTTATGGATTCTTACGCTCATTTCTACCATATTAGCAGTCTTTGCTGCTGTGTT
AATCATTTTCAGGAGAAGAATATCAGCATCCACAACGGAATGGCCTGTTGGCCCAAAAATTACCAATC
ATAGGTAACTTGCACATTCTTGGAGGCACTGCTCTCCATGTCGTCTTACATAAACTTGCTGAAGTTTA
CGGCAGTGTAATGACGATATGGATTGGTAGTTGGAAACCTGTTATTATTTTCCGACTTTGATCGAGCC
TGGGAAGTTCTTGTTAACAAATCGTCAGATTATTCAGCTCGTGAAATGCCTGAGATCACTAAAATCGG
CACTGCAAATTGGAGAACAATTTCAAGTTCTGATTCTGGCCTTTTGGGCCACTCTTCGAAAAGGTCTT
CAGAGTGTAGCATTATCGCCTCAGCATTTAGCATCGCAAACTGCACACCAAGAGAGAGATATAATAAA
GTTGATCAAAAATTTGAAAGACGAAGCAGTTCGGAATGGTTAAACCACTTGATCATCTCAAGAAAGCA
ACTGTAAGATTAATCAGTCGGTTAATCTATGGTCAGGATTTTGATGACGATAAGTATGTTGAAGATAT
GCATGACGTGATCGAGTTTTGATCGTATTAGTGGTTATGCTCAACTTGCTGAGGTATTCTATTATGCT
AAATATCTACCAGGTCATAAGAGAGCTGTAACTGGCGCCGAAGAAGCAAAAAGAAGAGTAATAGCTCT
GGTGCGTCCTTTCTCAGTCAAACCCTGCTACTAACACTTACTTGCATTTTCTCAAATCGCAACTGTAT
CCTGAAGAGGTTATCATATTCGCTATATTCGAAGCTTATCTTTTAGGTGTTGATAGCACTTCTTCAAC
ACTGCTGGGCACTCGCATTCTTAATACGCGAACCATCTGTTCAAGAGAAACTTTATCAAGAGCTTAAG
AATTTCACAGCCAATAACAATCGCACAATGCTGAAAGTCGAAGACGTCAACAAATTACATATTTCAAG
CTGTTGTTAAAGAAACAATGAGGATGAAACCAATTGCACCACTGGCGATTCCTCATAAAGCTTGTAAA
GACACTTCATTGATGGGCAAGAAAGTTGATAAGGGAACTAAAGTTATGTTAACATCATGCTTTACATC
ATACTGAAAAGGTTTGGAAAGAACCTTACAAATTCATACCAGAGAGGTTTCTGCAGAAGCACGATAAG
GCGATGGAACAATCACTATTACCATTTAGTGCAGGTAGAGAATTTGGCAGGAATGGAATTAGGAAAAC
TTCAGTTTAGTTTTTCTCTTGCTAATCTTGTTAATGCTTTTAAATGGTCTTGTGTGTCTGATGGAGTG
CTTCCTGATATGAGTGATTTACTGGGGTTGTTCTGTTATGAAAACCCCACTCGAAGCACGTATAGTTC
CTCGTTTGTAG

Figure 1c

ATGATGAACAAGTTATTATTTCTCCAACGGATTACTGATTCTCCTTCGACCACCATTATCAGTACTTT
TATTGTTACAATAATATCCATTGTTTTTCTCTACACTGTCTTGTTGATAAGGACGACTAAGAATAAGC
AGAAGATAGCAGCACCAAAAGCATCGGGGGCGTGGCCGTTCATAGGTCATCTCAAACTATTCATGAAA
CAAGATACTCAGTTTTACAGAACTCTAGGAACCATGTCTGATAAATACGGGTCGGTGTTCACACTTCG
ATTAGGAAACCAAGCAATCCTAGTTGTGAGCAACTGGGAGATGGTAAAAGAATGTTTCACAACAAACG
ACAAGTCATTCTCGAATCGTCCAAGTACGTTAAGCACTAAATACATGCTGAATGACACTAATTCTGTC
GTGTTTTCACCTTACGGAACGTATTGGAGAGAAATGCGGAAGATATTGGTGCAAAAACTACTGATCTC
TAACCAAAGATCAGAGGCATTGAAAAATCTGAAAACGAAAGAAATCGACAACTCGTTTGTAAAGCTTA
ATGATTTATGCAACAACGATGTCAGTGGAGGAGGCACAAAAGTTAGGATGGACGAATGGTTGGCTGAC
ATGATGTTCAACATTATTGCTAGGATTACATTTGGTTACCAAAGCGGAGGAGGCGATGCACCTGGCGC
TTCTACAACATCCAAGAATGTCGAGAGATACAAGAAAACGTTGGACGAGATGTTTGTTGTTTTAGCGA
CGAGGTTTGCAGTTTCAGATATATTTCCATCTCTGGAGTTTATAGACCGATTGAGAGGTCTTGTAAAG
GATATGAAAATCTTGGGAGACGAATTAAACTCCATTGCTGGATGTTTTATTGAAGAACATCGTCAAAA
GAGACGAGAATCATTATCCTCATTGTTATCTTTGTCAAATGAATCCGTTGGTGATGAACAAGATTTCA
TTGATGTTCTCTTGTCAATAATGGATCAGTCACGGCTTCCCGGAGATGACCCAGATTTTATTATCAAA
ATTATGATCCTGGAAGCTTTTGCAGGTGGGACGGACAGTTTAAGTGCAACCTTAACTTGGGTCCTCTC
TCTACTGCTGAACCACCCAAACGTGTTAAAGAGGGCAAGGGAGGAAATAGATAGGCATGTGGAAAACG
GTAAGCAAGTGGAAGTGTCTGATATTCCGAAGCTCGGATACATTGATGCAATAATCAAAGAGACGATG
AGATTGTATCCAGTCGGAGCATTAAGCGAACGATACACGACTGAAGAATGCGAGGTTGGTCGGTTTAA
CGTACCCGCTGGCACACGCTTACTGGTGAATATATGGAAGATCCACAGAGACCCAAGTGTGTGGGAGA
ATCCATCAGATTTTCAACCAGAGAGGTTTTTGTGCAGCGATAAGGTGGGTGTGGATTTATATGGCCAG
AATTATGAGCTGATACCATTTGGGGCCGGTAGGAGGGTATGTCCGGCTATAGTTTCATCACTGCAGAC
GATGCATTATGCGTTGGCGCGTCTTATTCAAGGATATGAAATGAAATCAGCCAGCCTCGATGGGAAGG
TGAATATGGAAGAAATGATAGCCATGTCGTGCCACAAGATGAGCCCTCTTGAAGTTATTATCAGTCCT
CGGGAGCCGAGGCGGAGTTAA

Figure 1d

ATGAACAAGTTATTATTTCTCCAACGGATTACTGATTCTCCTTCGACCACCATTATCAGTACTTTTAT
TGTTACAATAATATCCATTGTTTTTCTCTACACTGTCTTGTTGATAAGGACGACTAAGAATAAGCAGA
AGATAGCAGCACCAAAAGCATCGGGGGCGTGGCCGTTCATAGGTCATCTCAAACTATTCATGAAACAA
GATACTCAGTTTTACAGAACTCTAGGAACCATGTCTGATAAATACGGGTCGGTGTTCACACTTCGATT
AGGAAACCAAGCAATCCTAGTTGTGAGCAACTGGGAGATGGTAAAAGAATGTTTCACAACAAACGACA
AGTCATTCTCGAATCGTCCAAGTACGTTAAGCACTAAATACATGCTGAATGACACTAATTCTGTCGTG
TTTTCACCTTACGGAACGTATTGGAGAGAAATGCGGAAGATATTGGTGCAAAAACTACTGATCTCTAA
CCAAAGATCAGAGGCATTGAAAAATCTGAAAACGAAAGAAATCGACAACTCGTTTGTAAAGCTTAATG
ATTTATGCAACAACGATGTCAGTGGAGGAGGCACAAAAGTTAGGATGGACGAATGGTTGGCTGACATG
ATGTTCAACATTATTGCTAGGATTACATTTGGTTACCAAAGCGGAGGAGGCGATGCACCTGGCGCTTC
TACAACATCCAAGAATGTCGAGAGATACAAGAAAACGTTGGACGAGATGTTTGTTGTTTTAGCGACGA
GGTTTGCAGTTTCAGATATATTTCCATCTCTGGAGTTTATAGACCGATTGAGAGGTCTTGTAAAGGAT
ATGAAAATCTTGGGAGACGAATTAAACTCCATTGCTGGATGTTTTATTGAAGAACATCGTCAAAAGAG
ACGAGAATCATTATCCTCATTGTTATCTTTGTCAAATGAATCCGTTGGTGATGAACAAGATTTCATTG
ATGTTCTCTTGTCAATAATGGATCAGTCACGGCTTCCCGGAGATGACCCAGATTTTATTATCAAAATT
ATGATCCTGGAAGCTTTTGCAGGTGGGACGGACAGTTTAAGTGCAACCTTAACTTGGGTCCTCTCTCT
ACTGCTGAACCACCCAAACGTGTTAAAGAGGGCAAGGGAGGAAATAGATAGGCATGTGGAAAACGGTA
AGCAAGTGGAAGTGTCTGATATTCCGAAGCTCGGATACATTGATGCAATAATCAAAGAGACGATGAGA
TTGTATCCAGTCGGAGCATTAAGCGAACGATACACGACTGAAGAATGCGAGGTTGGTCGGTTTAACGT
ACCCGCTGGCACACGCTTACTGGTGAATATATGGAAGATCCACAGAGACCCAAGTGTGTGGGAGAATC
CATCAGATTTTCAACCAGAGAGGTTTTTGTGCAGCGATAAGGTGGGTGTGGATTTATATGGCCAGAAT
TATGAGCTGATACCATTTGGGGCCGGTAGGAGGGTATGTCCGGCTATAGTTTCATCACTGCAGACGAT
GCATTATGCGTTGGCGCGTCTTATTCAAGGATATGAAATGAAATCAGCCAGCCTCGATGGGAAGGTGA
ATATGGAAGAAATGATAGCCATGTCGTGCCACAAGATGAGCCCTCTTGAAGTTATTATCAGTCCTCGG
GAGCCGAGGCGGAGTTAA

Figure 3a

| Start | End | Feature |
|---|---|---|
| 1 | 130 | 5′ untranslated region |
| 131 | 800 | exon 1 |
| 801 | 881 | intron 1 |
| 882 | 1216 | exon 2 |
| 1059 | 1298 | intron 2 |
| 1299 | 1916 | exon 3 |
| 1917 | 1921 | 3′ untranslated region |

```
CTTGAGTCATGCCTTGATATGCTCATATTTTAGTTTGTCATATTCACTATAACTATAAATTTCAATAC
AATTTCTAAAACTCATCATCATTCAAGAGAGATACAAATACCTTGATATCCTTTTATCATCAATGGAG
TTATTCATAAAGTTACCATTTATCCAACCAATTCCTTTCAGTATTATTCTTGTTACTACAGTTTCGAT
TGTTCTATTATACAGTGTCTTCTTCTGGGTTACTGATAAGAAAAAGAAGAGGAAGAAAGCACCAAATG
CTGCAGGGGCATGGCCGTTAATAGGTCATCTCCGTCTATTGATGAACGACAAGGAACCGTTGTATAGA
GCACTAGGGAGCATGGCTGATAAGTACGGACCTGCATTCAACATCCGATTAGGTAACCAAGAAGTTCT
TGTTGTGAGTAACTGGGAGATGGTAAAACAGTGTTTTGGTAATCAAAATGATAAGCTATTTTCGAATC
GTCAAACTACATTAGCTGCAAAATACATGCTTAATCAAACAACTTCTAGCGGATTCGCACCATATGGA
CCATATTGGAGAGAGCTACGAAAGATAATGGTGCAGCAATTACTCTCTAAACAATCTTTAGAATCGTG
GAAACATCTGAAAATCAAAGAGATGGATGCTTCATTTAGTAAACTTAACGAGTTATGCAACAACAACG
GTACTGGAACAGCTACCCTAATTAGGATGGACGAATGGTTTGCTGAGTTGACGTTCAACGTGATCGCA
AGAAATGTCTTTGGCTACCAAAGTGGCGGAAGGTCGACAGCGCTTACGAACGGTAATATGATCATACT
CCCTCAATCTGTATCAATTTAAGGAAATCATTTTGGTCTTGTTATTAACTTGAATTTTCTATTAGGAG
ATACGGAATCAAAGGGCGAGAGGTACAAGAAAACATTGGAAGAAGCACTTCATCTTATGTCAATTTTT
GCAGTTTCAGACATATTTCCAAGTCTAGAGTGGGTAGATCGGTTAAGAGGCCTTATAAGGAATATGAA
ACGCTTTGGAGATGAGCTAAATTCAATTGCAGGGTGTCTTATTGAAGAGCACCGCCAAAAGAGATTAC
AATCCGTATCTAAAAGTGATAAAGGAGTTGGTGATGAACAAGACTTCGTTGATGTTCTCTTATCGGTT
GCTGAAAAATCGCAACTTCCTGGAGATGACCCTGATTTGGTCATCAAGTCTATGATTCTGGTTAGGCT
ATTGATACCAAGTCTATTGCAATTTTGGTTTATGTGCTTGTTCTAACTTTCGTTTACTGCATATGGAT
GTGCAGGAAATCGTATCAGGTGGGAGTGAGACCACATCGTCAACCTTAACTTGGGCCCTCTGTCTGTT
ACTGAACCATCCGCATGTGTTAAAGAAGGCAAAAGAGGAATTAGATACGCACGTAGGAAAAGATAGGC
ATGTAGAAGAGTCAGATACCCCTAAGCTCGTGTACATTAATGCAATTATCAAAGAATCAATGCGATTG
TATCCAAACGGGGCAATGCTTGATCGGTTGGCGTTAGAAGAGTGCGAAGTTGGTGGATTTCATGTACC
GGCCGGGGGACGCTTATTTGTCAATGTTTGGAAGATTCAGAGAGATCCGAGTGTTTGGGAGAATCCTC
TGGAGTTTAAACCAGAGAGGTGGTTTTTGAGTAATGGTGAAAAGATGGATGTGGATTACAAAGGTCAC
AATCATGAATTCATACCATTTGGGATAGGTCGGAGGATGTGCGCTGGTATGCTTTGGGCATCGGAGGT
GATTCATTTGGTGCTGCCCCGTCTTATTCATGGGTTTGATATGAAAGCAGCAAGTGCCAATGGGAAAG
TAGATATGGCAGAAATGGCAGGCATGGTGATTTGTTTTAAGAAGACACCTCTTGAAGTTATGGTCAAT
CCTCGAGAGTAGATGTT
```

Figure 3b

| Start | End | Feature |
|---|---|---|
| 1 | 69 | 5′ untranslated region |
| 70 | 1530 | ORF |
| 1531 | 1688 | 3′ untranslated region |

```
GATGAAATTCTTTATGCAAAGAGTCAATCTGACTCAAGCTAGCTAGAATATATACCAATCATAAAAGA
AATGATCATGAGTAACTTATGGATTCTTACGCTCATTTCTACCATATTAGCAGTCTTTGCTGCTGTGT
TAATCATTTTCAGGAGAAGAATATCAGCATCCACAACGGAATGGCCTGTTGGCCCAAAAACATTACCA
ATCATAGGTAACTTGCACATTCTTGGAGGCACTGCTCTCCATGTCGTCTTACATAAACTTGCTGAAGT
TTACGGCAGTGTAATGACGATATGGATTGGTAGTTGGAAACCTGTTATTATTGTTTCCGACTTTGATC
GAGCCTGGGAAGTTCTTGTTAACAAATCGTCAGATTATTCAGCTCGTGAAATGCCTGAGATCACTAAA
ATCGGCACTGCAAATTGGAGAACAATTTCAAGTTCTGATTCTGGTCCGTTTTGGGCCACTCTTCGAAA
AGGTCTTCAGAGTGTAGCATTATCGCCTCAGCATTTAGCATCGCAAACTGCACACCAAGAGAGAGATA
TAATAAAGTTGATCAAAAATTTGAAAGACGAAGCAGCTTCTGGAATGGTTAAACCACTTGATCATCTC
AAGAAAGCAACTGTAAGATTAATCAGTCGGTTAATCTATGGTCAGGATTTTGATGACGATAAGTATGT
TGAAGATATGCATGACGTGATCGAGTTTTTGATTCGTATTAGTGGTTATGCTCAACTTGCTGAGGTAT
TCTATTATGCTAAATATCTACCAGGTCATAAGAGAGCTGTAACTGGCGCCGAAGAAGCAAAAAGAAGA
GTAATAGCTCTGGTGCGTCCTTTTCTTCAGTCAAACCCTGCTACTAACACTTACTTGCATTTTCTCAA
ATCGCAACTGTATCCTGAAGAGGTTATCATATTCGCTATATTCGAAGCTTATCTTTTAGGTGTTGATA
GCACTTCTTCAACCACTGCATGGGCACTCGCATTCTTAATACGCGAACCATCTGTTCAAGAGAAACTT
TATCAAGAGCTTAAGAATTTCACAGCCAATAACAATCGCACAATGCTGAAAGTCGAAGACGTCAACAA
ATTACCATATTTACAAGCTGTTGTTAAAGAAACAATGAGGATGAAACCAATTGCACCACTGGCGATTC
CTCATAAAGCTTGTAAAGACACTTCATTGATGGGCAAGAAAGTTGATAAGGGAACTAAAGTTATGGTT
AACATTCATGCTTTACATCATACTGAAAAGGTTTGGAAAGAACCTTACAAATTCATACCAGAGAGGTT
TCTGCAGAAGCACGATAAGGCGATGGAACAATCACTATTACCATTTAGTGCAGGTATGAGAATTTGTG
CAGGAATGGAATTAGGAAAACTTCAGTTTAGTTTTTCTCTTGCTAATCTTGTTAATGCTTTTAAATGG
TCTTGTGTGTCTGATGGAGTGCTTCCTGATATGAGTGATTTACTGGGGTTTGTTCTGTTCATGAAAAC
CCCACTCGAAGCACGTATAGTTCCTCGTTTGTAGTGATGGAAATTTCATCTCATGTTGTTGTTTCTCT
TCATGTTTACTATTTCGTACTCGTTTGGTTTTGGTGTAAAAAATAAGATCTAAACTTCCAAATATCAT
TAATGTTTACACAAATCGAAATCAATCAACTATGTTATGAAAATTAGTGTTTTCGC
```

Figure 3c

| Start | End | Feature |
|---|---|---|
| 1 | 783 | promoter sequence |
| 784 | 905/908 | 5′ untranslated region |
| 906/909 | 1581 | exon 1 |
| 1582 | 1694 | intron 1 |
| 1695 | 2050 | exon 2 |
| 2051 | 2170 | intron 2 |
| 2171 | 2791 | exon 3 |
| 2792 | 2918 | 3′ untranslated region |

```
AAGTGTGCCACTAATCTACTGCTAGTGCTACTGCTCACTGACACTTACACATATGATTGATTTATGGC
TAAACAGGATGACCACTAAATTTATTTTGGAAAGCGGAGTGAATTAATTAAGTGGCACATTTTCCATG
AGAATTATTGATGGCATGCATTTAGATGAACAAGATACACCAAATGTAGTGACTGAACAAGATGCTCG
ATCCTAACCCCACCTGCAACTTTAGCTAAACTTTAATAATTACATGTCTTATCTTTTTATTGAATCAT
TTTATCTATCAATGGATGCTGATCAATAATATCATATATCTTTGCTTTTTCTTCAATCATTTAGATGA
ACAAAAAACACAATAAGTGTAGTGGTTGTTCATAACCCCACCTTCAACTCATTCTTCCCTTTAATAAC
AAATATCTTTGCTTTTTCTCCAATCATTTACTTGAACAACCAACACTAGTAAGTGTAGTGGTTTCTCA
TAACCCCACCTGCAATTTTTGCTTACCTTTAATAACATATATCTTTGATTTTCTTCGATCATTTTAGC
TACCAATGGATGCTGATCCAAAAAGTTATGGCAAAAAGAGACAACGTGATCGAACACGAGCCTCTCGT
GCACCACAGCATCAAGGTTTGTGGAAATTAACCGCTTGTAAAAAATGGAGTGCGTGATCATAATGAGG
TATTGCTAAGATATAGTATCAACTTTAGTGAACTGGGCCAACAAAACTCACGAGTTGTTGAAAATTGG
AGATTATATTTATAAGATAAAAGGGTCACTCCCTACACAACGACTTGCACTGCAAGTGAAAAAGAAAA
AAAACAAACAACCTCAATCTAGCTAGAGTCGTGAAAAAGTTTTGTGCGACTGTTATTTAGTTAATTAT
AAAATTTCAATGAAGTCGTTAATGATGAACAAGTTATTATTTCTCCAACGGATTACTGATTCTCCTTC
GACCACCATTATCAGTACTTTTATTGTTACAATAATATCCATTGTTTTTCTCTACACTGTCTTGTTGA
TAAGGACGACTAAGAATAAGCAGAAGATAGCAGCACCAAAAGCATCGGGGGCGTGGCCGTTCATAGGT
CATCTCAAACTATTCATGAAACAAGATACTCAGTTTTACAGAACTCTAGGAACCATGTCTGATAAATA
CGGGTCGGTGTTCACACTTCGATTAGGAAACCAAGCAATCCTAGTTGTGAGCAACTGGGAGATGGTAA
AAGAATGTTTCACAACAAACGACAAGTCATTCTCGAATCGTCCAAGTACGTTAAGCACTAAATACATG
CTGAATGACACTAATTCTGTCGTGTTTTCACCTTACGGAACGTATTGGAGAGAAATGCGGAAGATATT
GGTGCAAAAACTACTGATCTCTAACCAAAGATCAGAGGCATTGAAAAATCTGAAAACGAAAGAAATCG
ACAACTCGTTTGTAAAGCTTAATGATTTATGCAACAACGATGTCAGTGGAGGAGGCACAAAAGTTAGG
ATGGACGAATGGTTGGCTGACATGATGTTCAACATTATTGCTAGGATTACATTTGGTTACCAAAGCGG
AGGAGGCGATGCACCTGGTATGTGATCATCAAATTTTCGTTAAAACCAAATTAACTTGTACTATATCT
TATGTTTACATGTTATATTGATCACTTTGACACGTTCTGATCATTTTCACAAATCGAATTAGGCGCTT
CTACAACATCCAAGAATGTCGAGAGATACAAGAAAACGTTGGACGAGATGTTTGTTGTTTTAGCGACG
AGGTTTGCAGTTTCAGATATATTTCCATCTCTGGAGTTTATAGACCGATTGAGAGGTCTTGTAAAGGA
TATGAAAATCTTGGGAGACGAATTAAACTCCATTGCTGGATGTTTTATTGAAGAACATCGTCAAAAGA
GACGAGAATCATTATCCTCATTGTTATCTTTGTCAAATGAATCCGTTGGTGATGAACAAGATTTCATT
GATGTTCTCTTGTCAATAATGGATCAGTCACGGCTTCCCGGAGATGACCCAGATTTTATTATCAAAAT
TATGATCCTGGTAACATATATTACAACAGTATTTCTTTAAGTTATGGATTAATGGATGTCGTAACCAT
GAATATTTTTCTGATCTGGATAAATGTAATCCGGAACTAATATATGAATATTGTTGACGCAGGAAGCT
TTTGCAGGTGGGACGGACAGTTTAAGTGCAACCTTAACTTGGGTCCTCTCTCTACTGCTGAACCACCC
AAACGTGTTAAAGAGGGCAAGGGAGGAAATAGATAGGCATGTGGAAAACGGTAAGCAAGTGGAAGTGT
CTGATATTCCGAAGCTCGGATACATTGATGCAATAATCAAAGAGACGATGAGATTGTATCCAGTCGGA
GCATTAAGCGAACGATACACGACTGAAGAATGCGAGGTTGGTCGGTTTAACGTACCCGCTGGCACACG
CTTACTGGTGAATATATGGAAGATCCACAGAGACCCAAGTGTGTGGGAGAATCCATCAGATTTTCAAC
CAGAGAGGTTTTTGTGCAGCGATAAGGTGGGTGTGGATTTATATGGCCAGAATTATGAGCTGATACCA
TTTGGGGCCGGTAGGAGGGTATGTCCGGCTATAGTTTCATCACTGCAGACGATGCATTATGCGTTGGC
GCGTCTTATTCAAGGATATGAAATGAAATCAGCCAGCCTCGATGGGAAGGTGAATATGGAAGAAATGA
TAGCCATGTCGTGCCACAAGATGAGCCCTCTTGAAGTTATTATCAGTCCTCGGGAGCCGAGGCGGAGT
TAAATCTTATGTTCCAATTTTACATTAGCATCTTTGATTATGAAATGTATTGCTCTTAAGTTTCTTTT
TTGTTTTTTATATTTTTAAGCTTGTATGTGATCATCAGCGAAAATGATGATGACAGAATCGT
```

Figure 4a

MELFIKLPFIQPIPFSIILVTTVSIVLLYSVFFWVTDKKKKRKKAPNAAGAWPLIGHLRLLMNDKEPL
YRALGSMADKYGPAFNIRLGNQEVLVVSNWEMVKQCFGNQNDKLFSNRQTTLAAKYMLNQTTSSGFAP
YGPYWRELRKIMVQQLLSKQSLESWKHLKIKEMDASFSKLNELCNNNGTGTATLIRMDEWFAELTFNV
IARNVFGYQSGGRSTALTNGDTESKGERYKKTLEEALHLMSIFAVSDIFPSLEWVDRLRGLIRNMKRF
GDELNSIAGCLIEEHRQKRLQSVSKSDKGVGDEQDFVDVLLSVAEKSQLPGDDPDLVIKSMILEIVSG
GSETTSSTLTWALCLLLNHPHVLKKAKEELDTHVGKDRHVEESDTPKLVYINAIIKESMRLYPNGAML
DRLALEECEVGGFHVPAGGRLFVNVWKIQRDPSVWENPLEFKPERWFLSNGEKMDVDYKGHNHEFIPF
GIGRRMCAGMLWASEVIHLVLPRLIHGFDMKAASANGKVDMAEMAGMVICFKKTPLEVMVNPRE.

Figure 4b

MIMSNLWILTLISTILAVFAAVLIIFRRRISASTTEWPVGPKTLPIIGNLHILGGTALHVVLHKLAEV
YGSVMTIWIGSWKPVIIVSDFDRAWEVLVNKSSDYSAREMPEITKIGTANWRTISSSDSGPFWATLRK
GLQSVALSPQHLASQTAHQERDIIKLIKNLKDEAASGMVKPLDHLKKATVRLISRLIYGQDFDDDKYV
EDMHDVIEFLIRISGYAQLAEVFYYAKYLPGHKRAVTGAEEAKRRVIALVRPFLQSNPATNTYLHFLK
SQLYPEEVIIFAIFEAYLLGVDSTSSTTAWALAFLIREPSVQEKLYQELKNFTANNNRTMLKVEDVNK
LPYLQAVVKETMRMKPIAPLAIPHKACKDTSLMGKKVDKGTKVMVNIHALHHTEKVWKEPYKFIPERF
LQKHDKAMEQSLLPFSAGMRICAGMELGKLQFSFSLANLVNAFKWSCVSDGVLPDMSDLLGFVLFMKT
PLEARIVPRL.

Figure 4c

MMNKLLFLQRITDSPSTTIISTFIVTIISIVFLYTVLLIRTTKNKQKIAAPKASGAWPFIGHLKLFMK
QDTQFYRTLGTMSDKYGSVFTLRLGNQAILVVSNWEMVKECFTTNDKSFSNRPSTLSTKYMLNDTNSV
VFSPYGTYWREMRKILVQKLLISNQRSEALKNLKTKEIDNSFVKLNDLCNNDVSGGGTKVRMDEWLAD
MMFNIIARITFGYQSGGGDAPGASTTSKNVERYKKTLDEMFVVLATRFAVSDIFPSLEFIDRLRGLVK
DMKILGDELNSIAGCFIEEHRQKRRESLSSLLSLSNESVGDEQDFIDVLLSIMDQSRLPGDDPDFIIK
IMILEAFAGGTDSLSATLTWVLSLLLNHPNVLKRAREEIDRHVENGKQVEVSDIPKLGYIDAIIKETM
RLYPVGALSERYTTEECEVGRFNVPAGTRLLVNIWKIHRDPSVWENPSDFQPERFLCSDKVGVDLYGQ
NYELIPFGAGRRVCPAIVSSLQTMHYALARLIQGYEMKSASLDGKVNMEEMIAMSCHKMSPLEVIISP
REPRRS.

Figure 4d

MNKLLFLQRITDSPSTTIISTFIVTIISIVFLYTVLLIRTTKNKQKIAAPKASGAWPFIGHLKLFMKQ
DTQFYRTLGTMSDKYGSVFTLRLGNQAILVVSNWEMVKECFTTNDKSFSNRPSTLSTKYMLNDTNSVV
FSPYGTYWREMRKILVQKLLISNQRSEALKNLKTKEIDNSFVKLNDLCNNDVSGGGTKVRMDEWLADM
MFNIIARITFGYQSGGGDAPGASTTSKNVERYKKTLDEMFVVLATRFAVSDIFPSLEFIDRLRGLVKD
MKILGDELNSIAGCFIEEHRQKRRESLSSLLSLSNESVGDEQDFIDVLLSIMDQSRLPGDDPDFIIKI
MILEAFAGGTDSLSATLTWVLSLLLNHPNVLKRAREEIDRHVENGKQVEVSDIPKLGYIDAIIKETMR
LYPVGALSERYTTEECEVGRFNVPAGTRLLVNIWKIHRDPSVWENPSDFQPERFLCSDKVGVDLYGQN
YELIPFGAGRRVCPAIVSSLQTMHYALARLIQGYEMKSASLDGKVNMEEMIAMSCHKMSPLEVIISPR
EPRRS

Figure 8a

| GSK NOSCAPINE CVS1 x GSK THEBAINE CVS1 | | | | |
|---|---|---|---|---|
| SUM | Noscapine + | | Noscapine - | |
| 275 | 61 | | 214 | |
| | *PSCYP1* + | *PSCYP1* - | *PSCYP1* + | *PSCYP1* - |
| | 61 | 0 | 129 | 85 |
| SUM | *PSCYP1* + | | *PSCYP1* - | |
| 275 | 190 | | 85 | |
| | Noscapine + | Noscapine - | Noscapine + | Noscapine - |
| | 61 | 129 | 0 | 85 |

Figure 8b

| GSK NOSCAPINE CVS1 x GSK THEBAINE CVS1 | | | | |
|---|---|---|---|---|
| SUM | Noscapine + | | Noscapine - | |
| 275 | 61 | | 214 | |
| | *PSCYP2* + | *PSCYP2* - | *PSCYP2* + | *PSCYP2* - |
| | 61 | 0 | 129 | 85 |
| SUM | *PSCYP2* + | | *PSCYP2* - | |
| 275 | 190 | | 85 | |
| | Noscapine + | Noscapine - | Noscapine + | Noscapine - |
| | 61 | 129 | 0 | 85 |

Figure 8c

| GSK NOSCAPINE CVS1 x GSK THEBAINE CVS1 | | | | |
|---|---|---|---|---|
| SUM | Noscapine + | | Noscapine - | |
| 259 | 59 | | 200 | |
| | *PSCYP3* + | *PSCYP3*- | *PSCYP3* + | *PSCYP3* - |
| | 59 | 0 | 122 | 78 |
| SUM | *PSCYP3* + | | *PSCYP3*- | |
| 259 | 181 | | 78 | |
| | Noscapine + | Noscapine - | Noscapine + | Noscapine - |
| | 59 | 122 | 0 | 78 |

the *PSCYP3* genotyping assay failed on 16 samples; these were excluded from the analysis

Figure 9

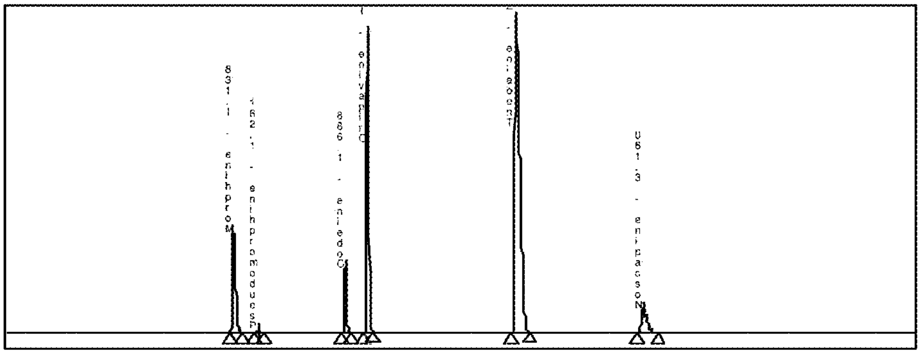

Figure 10

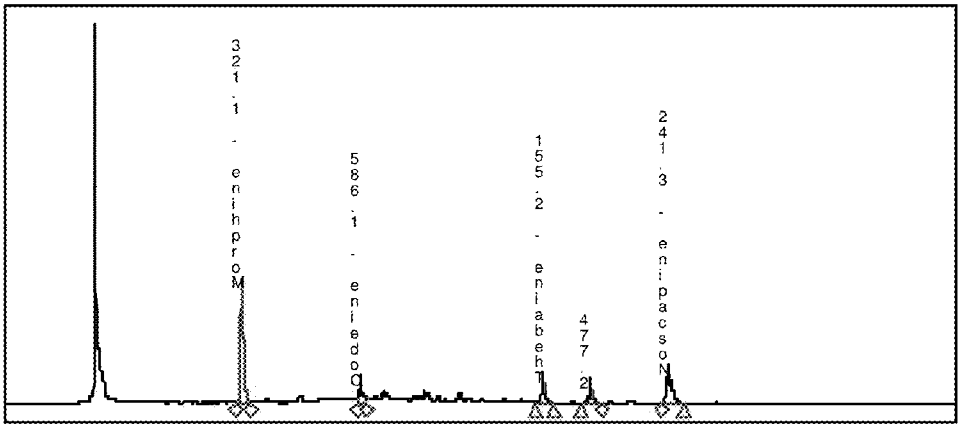

Figure 11

GAGGTGTTCATTGCCATGTCAAAGGCATTAAACTTCATAAACCCAGATGAGCTTTCGATGCAGTGCAT
TTTGATAGCTTTGAACCGTTTCCTTCAGGAAAAGCATGGTTCCAAGATGGCCTTTTTAGATGGTAATC
CTCCCGAGAGACTTTGCAAGCCGGTCGTGGATCATATAGAGTCACTTGGCGGTGAAGTCCGTCTCAAT
TCCAGGATTAAAAAGATTGAGCTTAAAAAAGATGGTACTGTGAAACGTCTAATGCTCACCAACGGTGA
TGCAATAGAAGGAGATGCTTATGTCATTGCAACCCCAGTGGACATCCTAAAGCTGCTTATACCCGAGG
AGTGGAAAGAAGTTGGGTACTTTAAAAGATTGGATAAATTAGTTGGAGTTCCTGTGATTAACGTCCAT
ATATGGTTTGACAGGAAATTGAAAAATACATATGATCATCTTCTCTTCAGCAGAAGTCCCCTCTTAAG
CGTATACGCTGACATGTCAGTGACATGCAAGGAATATTATGACCCAAACAAATCCATGCTTGAGTTGG
TATTTGCACCCGCTGAGGAATGGATCTCGCGCAGTGACTCTGAAATTATTGAAGCTACTATGCAGGAG
CTTGCGAAAC

Figure 12

ATGATCATGAGTAACTTATGGATTCTTACGCTCATTTCTACCATATTAGCAGTCTTTGCTGCTGTGTT
AATCATTTTCAGGAGAAGAATATCAGCATCCACAACGGAATGGCCTGTTGG

Figure 13

TAGGAGGGTATGTCCGGCTATAGTTTCATCACTGCAGACGATGCATTATGCGTTGGCGCGTCTTATTC
AAGGATATGAAATGAAATCAGCCAGCCTCGATGGGAAGGTGAATATGGAAGAAATGATAGCCATGTCG
TGCCACAAGATGAGCCCTCTTGAAGTTATTATCAGTCCTCGGGAGCCGAGGCGGAGTTAA

PLANT CYTOCHROME P450

CROSS-REFERENCE TO RELATED APPLICATIONS

This is a divisional of U.S. patent application Ser. No. 13/806,608 filed Dec. 21, 2012, which is the U.S. National Stage of International Application No. PCT/GB2011/051340, filed Jul. 18, 2011, which was published in English under PCT Article 21(2), which in turn claims the benefit of Great Britain Application No. 1012262.0, filed Jul. 22, 2010 and Great Britain Application No. 1021707.3, filed Dec. 22, 2010.

INTRODUCTION

This disclosure relates to the isolation and sequencing of nucleic acid molecules that encode novel cytochrome P450s from a *Papaver somniferum* cultivar, [poppy plant]; transgenic cells transformed with said nucleic acid molecules, sequence variants of the gene; the use of said genes/proteins in the production of noscapine and the use of the genes as a marker of poppy plants that synthesize noscapine.

BACKGROUND

Plant cytochrome P450s are a very large family of enzymes responsible for the oxidation, peroxidation and reduction of a vast number of plant intermediate metabolites such as alkaloids, terpenoids, lipids, glycosides and glucosinolates. P450s are known to be involved in the metabolism and detoxification of pesticides as well as the biosynthesis of primary and secondary metabolites.

Plant cytochrome P450s are known in the art and have been successfully cloned, expressed and characterized. For example, WO2009/064771 and WO2008/070274, each disclose cytochrome P450 genes and their use in the alteration of alkaloid content in *Nicotiana tabacum*. These patent applications describe how the inhibition of specific P450s reduces the amount of N' nitrosonornicotine, a known carcinogen, in planta. WO2008/150473 discloses the over expression of cytochrome P450s to confer resistance or tolerance to herbicides, in particular, benzothiadiazones and sulfonylureas. In WO2008/088161 is disclosed transgenic plants that over express a cytochrome P450 which results in increased seed size or the storage protein content of seeds. The over expression also confers increased water stress resistance. What is apparent is that plant cytochrome P450s have diverse functions in regulating the biochemical activities in plant cells and are known in the art.

The opium poppy *P. somniferum* is the plant from which opium is extracted. The opium poppy is the only commercially exploited poppy of the family Papaveraceae and is the principal source of natural opiates. The opium is extracted from latex harvested from the green seed pods. A further source of opiate alkaloids is the poppy straw which is the dried mature plant. *P. somniferum* is a source of clinically useful opiate alkaloids such as morphine, codeine, thebaine, noscapine [also known as narcotine] and papaverine. The clinical application of these opiate alkaloids and their derivates is broad having use as analgesics, cough suppressants and anti-spasmodics. Although not used as a pharmacological agent in its own right, thebaine is a particularly useful opiate which can be converted into a range of compounds such as hydrocodone, oxycodone, oxymorphone, nalbuphine naltrexone, buprenorphine and etorphine. These intermediates also have broad pharmaceutical applications. For example, oxycodone, oxymorphone and etorphine are widely used as an analgesic for moderate to severe pain and are often combined with other analgesics such as ibuprofen. Buprenorphine is used in the treatment of heroin addiction and chronic pain. Naltrexone is used in the treatment of alcohol and opiate addiction.

This disclosure relates to the identification and characterization of cytochrome P450s isolated from a *Papaver somniferum* cultivar we call PSCYP1, PSCYP2 and PSCYP3. The predicted protein encoded by PSCYP1 exhibits highest sequence identity to a cytochrome P450 from *Coptis japonica* (GenBank accession no. BAF98472.1, 46% identity). The closest homologue with an assignment to a cytochrome P450 subfamily is CYP82C4 from *Arabidopsis lyrata* (NCBI reference seq no. XP_002869304.1, 44% identity). The *Arabidopsis thaliana* CYP82C4 protein has been shown to add a hydroxyl group to the 5 position of 8-methoxypsoralen, a furocoumarin, creating 5-hydroxy-8-methoxypsoralen (Kruse et al. (2008) Chemistry & Biology 15: 149-156). The closest homologues of the predicted protein encoded by PSCYP2 are annotated as stylopine synthases from *Argemone mexicana* (GenBank accession no. ABR14721, 77% identity), *Papaver somniferum* (GenBank accession no ADB89214, 76% identity) and *Eschscholzia californica* (GenBank accession no. BAD98250, 72% identity). They belong to the CYP719A subfamily of cytochrome P450s which have only been found in isoquinoline alkaloid-producing plant species where they catalyse the formation of methylenedioxy-bridges (Ikezawa et al. (2009) Plant Cell Rep. 28:123-133). The closest homologue of the predicted protein encoded by PSCYP3 is annotated as protopine 6-hydroxylase from *Eschscholzia californica* (GenBank accession no. BAK20464, 44% identity). The closest homologue with an assignment to a cytochrome P450 subfamily is CYP82C4 from *Arabidopsis lyrata* mentioned above (42% identity). Surprisingly PSCYP1, PSCYP2 and PSCYP3 are unique to *Papaver somniferum* cultivars that produce noscapine. Those cultivars that do not produce noscapine do not include this gene.

STATEMENTS OF INVENTION

According to an aspect of the invention there is provided an isolated nucleic acid molecule that encodes a cytochrome P450 polypeptide wherein said nucleic acid molecule comprises or consists of a nucleotide sequence selected from the group consisting of:

i) a nucleotide sequence as represented by the sequence in FIG. 1*a*, 1*b*, 1*c*, 1*d*, 3*a*, 3*b* or 3*c*;

ii) a nucleotide sequence wherein said sequence is degenerate as a result of the genetic code to the nucleotide sequence defined in (i);

iii) a nucleic acid molecule the complementary strand of which hybridizes under stringent hybridization conditions to the sequence in FIG. 1*a*, 1*b*, 1*c*, 1*d*, 3*a*, 3*b* or 3*c* wherein said nucleic acid molecule encodes a cytochrome P450 polypeptide;

iv) a nucleotide sequence that encodes a polypeptide comprising an amino acid sequence as represented in FIG. 4*a*, 4*b*, 4*c* or 4*d*;

v) a nucleotide sequence that encodes a polypeptide comprising an amino acid sequence wherein said amino acid sequence is modified by addition deletion or substitution of at least one amino acid residue as represented in iv) above and which has retained or enhanced cytochrome P450 activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Allows Sequences that Share at Least 80% Identity to Hybridize)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Allows Sequences that Share at Least 50% Identity to Hybridize)

Hybridization: 6×SSC at RT to 55° C. for 16-20 hours

Wash at least twice: 2×-3×SSC at RT to 55° C. for 20-30 minutes each.

In a preferred embodiment of the invention said nucleic acid molecule comprises or consists of a nucleotide sequence as represented in FIG. 1*a*, 1*b*, 1*c* or 1*d*.

According to a further aspect of the invention there is provided an isolated polypeptide selected from the group consisting of:

i) a polypeptide comprising or consisting of an amino acid sequence as represented in FIG. 4*a*, 4*b*, 4*c* or 4*d*; or ii) a modified polypeptide comprising or consisting of a modified amino acid sequence wherein said polypeptide is modified by addition deletion or substitution of at least one amino acid residue of the sequence presented in FIG. 4*a*, 4*b*, 4*c* or 4*d* and which has retained or enhanced cytochrome P450 activity.

A modified polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 43%, 45%, or 47% identity, more preferably at least 50% identity, still more preferably at least 60%, 65%, 70%, 75%, 80%, 85%, 90%, 95% identity, and at least 99% identity with the full length amino acid sequence illustrated herein.

According to a further aspect of the invention there is provided a vector comprising a nucleic acid molecule encoding a cytochrome P450 polypeptide according to the invention wherein said nucleic acid molecule is operably linked to a nucleic acid molecule comprising a promoter sequence.

In a preferred embodiment of the invention said nucleic acid sequence comprising a promoter confers constitutive expression on said cytochrome P450 polypeptide.

In an alternative preferred embodiment of the invention said nucleic acid molecule comprising a promoter confers regulated expression on said cytochrome P450 polypeptide.

In a preferred embodiment of the invention said regulated expression is tissue or developmentally regulated expression.

In a further alternative embodiment of the invention said regulated expression is inducible expression.

In an alternative embodiment of the invention a vector including a nucleic acid molecule according to the invention need not include a promoter or other regulatory sequence, particularly if the vector is to be used to introduce the nucleic acid molecule into cells for recombination into the gene.

Preferably the nucleic acid molecule in the vector is under the control of, and operably linked to, an appropriate promoter or other regulatory elements for transcription in a host cell such as a microbial, (e.g. bacterial, yeast), or plant cell. The vector may be a bi-functional expression vector which functions in multiple hosts. In the case of cytochrome P450 genomic DNA this may contain its own promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18: (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997) Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter.

Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809).

If desired, selectable genetic markers may be included in the construct, such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

According to a further aspect of the invention there is provided a transgenic cell transformed or transfected with a nucleic acid molecule or vector according to the invention.

In a preferred embodiment of the invention said cell is a plant cell.

In a preferred embodiment of the invention said plant cell is from the family Papaveraceae.

In a preferred embodiment of the invention said plant cell is a *Papaver somniferum* cell.

According to a further aspect of the invention there is provided a plant comprising a plant cell according to the invention.

In a preferred embodiment of the invention said plant is from the family Papaveraceae; preferably *Papaver somniferum.*

In an alternative preferred embodiment of the invention said cell is a microbial cell; preferably a bacterial or fungal cell [e.g. yeast, *Saccharomyces cerevisiae].*

In a preferred embodiment of the invention said cell is adapted such that the nucleic acid molecule encoding the cytochrome P450 is over-expressed when compared to a non-transgenic cell of the same species.

According to a further aspect of the invention there is provided a nucleic acid molecule comprising a transcription cassette wherein said cassette includes a nucleotide sequence designed with reference to FIG. 1*a*, 1*b*, 1*c* or 1*d* and is adapted for expression by provision of at least one promoter operably linked to said nucleotide sequence such that both sense and antisense molecules are transcribed from said cassette.

In a preferred embodiment of the invention said cassette is adapted such that both sense and antisense ribonucleic acid molecules are transcribed from said cassette wherein said sense and antisense nucleic acid molecules are adapted to anneal over at least part or all of their length to form a small interfering RNA [siRNA] or short hairpin RNA [shRNA].

In a preferred embodiment of the invention said cassette is provided with at least two promoters adapted to transcribe both sense and antisense strands of said ribonucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an ribonucleic acid molecule which forms a double stranded region by complementary base pairing of said first and second parts thereby forming an shRNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of said cytochrome P450 polypeptide.

According to an aspect of the invention there is provided a process for the modification of an opiate alkaloid comprising:

i) providing a transgenic plant cell according to the invention;
ii) cultivating said plant cell to produce a transgenic plant; and optionally
i) harvesting said transgenic plant, or part thereof.

In a preferred method of the invention said harvested plant material is dried straw and said opiate alkaloid is extracted.

According to an alternative aspect of the invention there is provided a process for the modification of an opiate alkaloid comprising:

i) providing a transgenic microbial cell according to the invention that expresses a cytochrome P450 according to the invention in culture with at least one opiate alkaloid;
ii) cultivating the microbial cell under conditions that modify one or more opiate alkaloids; and optionally
iii) isolating said modified alkaloid from the microbial cell or cell culture.

In a preferred method of the invention said microbial cell is a bacterial cell or fungal/yeast cell.

If microbial cells are used as organisms in the process according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The methylated opiate alkaloids produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIEGO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the opiate alkaloids present therein.

According to a further aspect of the invention there is provided the use of a gene encoded by a nucleic acid molecule as represented by the nucleic acid sequence in FIG. 3*a*, 3*b* or 3*c*, or a nucleic acid molecule that hybridizes under stringent hybridization conditions to the nucleotide sequence in FIG. 3*a*, 3*b* or 3*c* and encodes a polypeptide with cytochrome P450 activity as a means to identify the presence or absence of a gene that encodes said cytochrome P450 in a Papaveraceae plant.

According to a further aspect of the invention there is provided a method to determine the presence or absence of a gene according to the invention in a Papaveraceae variety comprising:

i) obtaining a sample from a Papaveraceae plant;
ii) extracting genomic DNA from the plant; and
iii) analyzing the genomic DNA for the presence of a gene comprising or consisting of a nucleotide sequence as represented in FIG. 3*a*, 3*b* or 3*c*.

Methods to analyze genomic DNA are well known in the art. For example, polymerase chain reaction methods using sequence specific oligonucleotide primers to amplify specific regions of the gene according to the invention. The extraction, isolation and restriction analysis using sequence specific restriction endonucleases followed by separation and Southern blotting to analyze genomic structure have been established for over thirty years. The analysis may be directed to intron or exon structure or upstream or downstream regions of the gene; e.g. promoter regions.

According to a further aspect of the invention there is provided the use of a gene encoded by a nucleic acid molecule as represented by the nucleic acid sequence in FIG. 3*a*, 3*b* or 3*c*, or a nucleic acid molecule that hybridizes under stringent hybridization conditions to the nucleotide sequence in FIG. 3*a*, 3*b* or 3*c* and encodes a polypeptide with cytochrome P450 activity as a means to identify a locus wherein said locus is associated with altered expression or activity of said cytochrome P450.

Mutagenesis as a means to induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, psoralen exposure combined with UV irradiation].

According to a further aspect of the invention there is provided a method to produce a Papaveraceae plant variety that has altered expression of a cytochrome P450 polypeptide according to the invention comprising the steps of:

i) mutagenesis of wild-type seed from a plant that does express said cytochrome P450 polypeptide;
ii) cultivation of the seed in i) to produce first and subsequent generations of plants;
iii) obtaining seed from the first generation plant and subsequent generations of plants;
iv) determining if the seed from said first and subsequent generations of plants has altered nucleotide sequence and/or altered expression of said cytochrome P450 polypeptide;
v) obtaining a sample and analysing the nucleic acid sequence of a nucleic acid molecule selected from the group consisting of:
   a) a nucleic acid molecule comprising a nucleotide sequence as represented in FIG. 3*a*, 3*b* or 3*c;*
   b) a nucleic acid molecule that hybridises to the nucleic acid molecule in a) under stringent hybridisation conditions and that encodes a polypeptide with cytochrome P450 polypeptide activity; and optionally
vi) comparing the nucleotide sequence of the nucleic acid molecule in said sample to a nucleotide sequence of a nucleic acid molecule of the original wild-type plant.

In a preferred method of the invention said nucleic acid molecule is analysed by a method comprising the steps of:

i) extracting nucleic acid from said mutated plants;
ii) amplification of a part of said nucleic acid molecule by a polymerase chain reaction;
iii) forming a preparation comprising the amplified nucleic acid and nucleic acid extracted from wild-type seed to form heteroduplex nucleic acid;
iv) incubating said preparation with a single stranded nuclease that cuts at a region of heteroduplex nucleic acid to identify the mismatch in said heteroduplex; and
v) determining the site of the mismatch in said nucleic acid heteroduplex.

In a preferred method of the invention said Papaveraceae plant variety has enhanced cytochrome P450 polypeptide expression and/or activity.

According to a further aspect of the invention there is provided a plant obtained by the method according to the invention.

According to an aspect of the invention there is provided a plant wherein said plant comprises a viral vector that includes all or part of a gene comprising a nucleic acid molecule according to the invention.

In a preferred embodiment of the invention said gene is encoded by a nucleic acid molecule comprising a nucleic acid sequence selected from the group consisting of:

i) a nucleic acid molecule comprising a nucleotide sequence as represented in FIG. 1*a*, 1*b*, 1*c* or 1*d;*
ii) a nucleic acid molecule comprising a nucleotide sequence that hybridises under stringent hybridisation conditions to a nucleic acid molecule in (i) and which encodes a cytochrome p450 polypeptide;
iii) a nucleic acid molecule that encodes a variant polypeptide that varies from a polypeptide comprising the amino acid sequence as represented in FIG. 4*a*, 4*b*, 4*c*, or 4*d*.

In a preferred embodiment of the invention said nucleic acid molecule comprises or consists of a nucleotide sequence as represented in FIG. 1*a*.

In a preferred embodiment of the invention said nucleic acid molecule comprises or consists of a nucleotide sequence as represented in FIG. 1*b*.

In a preferred embodiment of the invention said nucleic acid molecule comprises or consists of a nucleotide sequence as represented in FIG. 1*c*

In a preferred embodiment of the invention said nucleic acid molecule comprises or consists of a nucleotide sequence as represented in FIG. 1*d*.

In a preferred embodiment of the invention said nucleic acid molecule consists of a nucleotide sequence as represented in FIG. 12.

In an alternative preferred embodiment of the invention said nucleic acid molecule consists of a nucleotide sequence as represented in FIG. 13.

According to a further aspect of the invention there is provided a viral vector comprising all or part of a nucleic acid molecule according to the invention.

According to an aspect of the invention there is provided the use of a viral vector according to the invention in viral induced gene silencing in a plant.

In a preferred embodiment of the invention said plant is from the family Papaveraceae.

Virus induced gene silencing [VIGS] is known in the art and exploits a RNA mediated antiviral defence mechanism. Plants that are infected with an unmodified virus induce a mechanism that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1*a* (SEQ ID NO: 1) is nucleotide sequence of a cDNA that encodes PSCYP1, FIG. 1*b* (SEQ ID NO: 2) is nucleotide sequence of a cDNA that encodes PSCYP2, FIG. 1*c* (SEQ ID NO: 3) is nucleotide sequence of a cDNA that encodes PSCYP3; FIG. 1*d* (SEQ ID NO: 4) is nucleotide sequence of another embodiment of a cDNA that encodes PSCYP3;

FIG. 2*a* illustrates the frequency of ESTs of the PSCYP1 gene in EST libraries derived from 454 sequencing of stem and capsule tissues from cultivars GSK MORPHINE CVS1, GSK MORPHINE CVS2, GSK NOSCAPINE CVS1 and GSK THEBAINE CVS1. The 16 EST libraries were generated by pyrosequencing using cDNA libraries prepared from stems (S) and capsules (C) at two developmental stages 'early harvest' (EH, 1-3 days after petals had fallen off) and 'late-harvest' (LH, 4-6 days after petals had fallen off) from each of the four *P. somniferum* cultivars; FIG. 2*b* illustrates the frequency of ESTs of the PSCYP2 gene; FIG. 2*c* illustrates the frequency of ESTs of the PSCYP3 gene;

FIG. 3*a* (SEQ ID NO: 5) is the nucleotide sequence of the gene encoding PSCYP1; FIG. 3*b* (SEQ ID NO: 6) is the nucleotide sequence of the gene encoding PSCYP2, FIG. 3*c* (SEQ ID NO: 7) is the nucleotide sequence of the gene encoding PSCYP3;

FIG. 4*a* (SEQ ID NO: 8) is the deduced amino acid sequence of PSCYP1; FIG. 4*b* (SEQ ID NO: 9) is the deduced amino acid sequence of PSCYP2; FIG. 4*c* (SEQ ID NO: 10) is the deduced amino acid sequence of PSCYP3; FIG. 4*d* (SEQ ID NO: 11) is the deduced amino acid sequence of PSCYP3;

Figure 14:
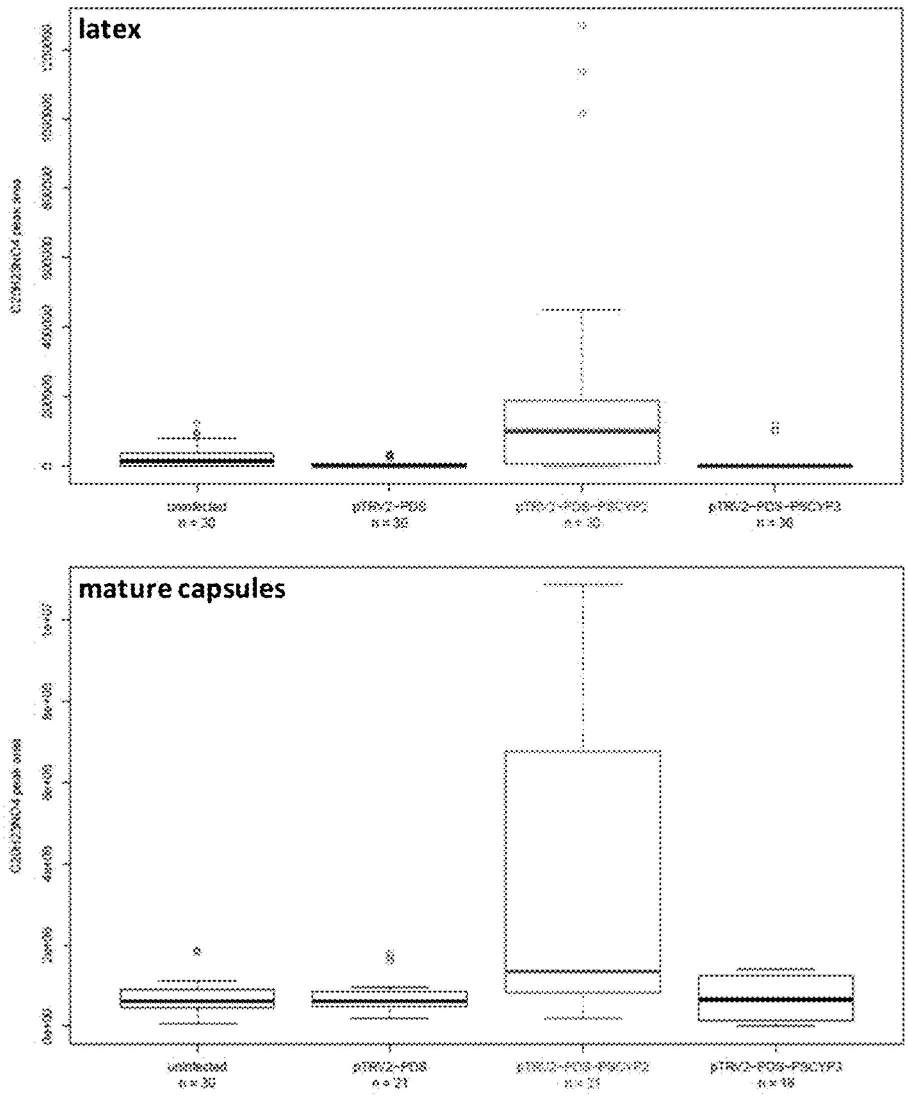
Figure 15:
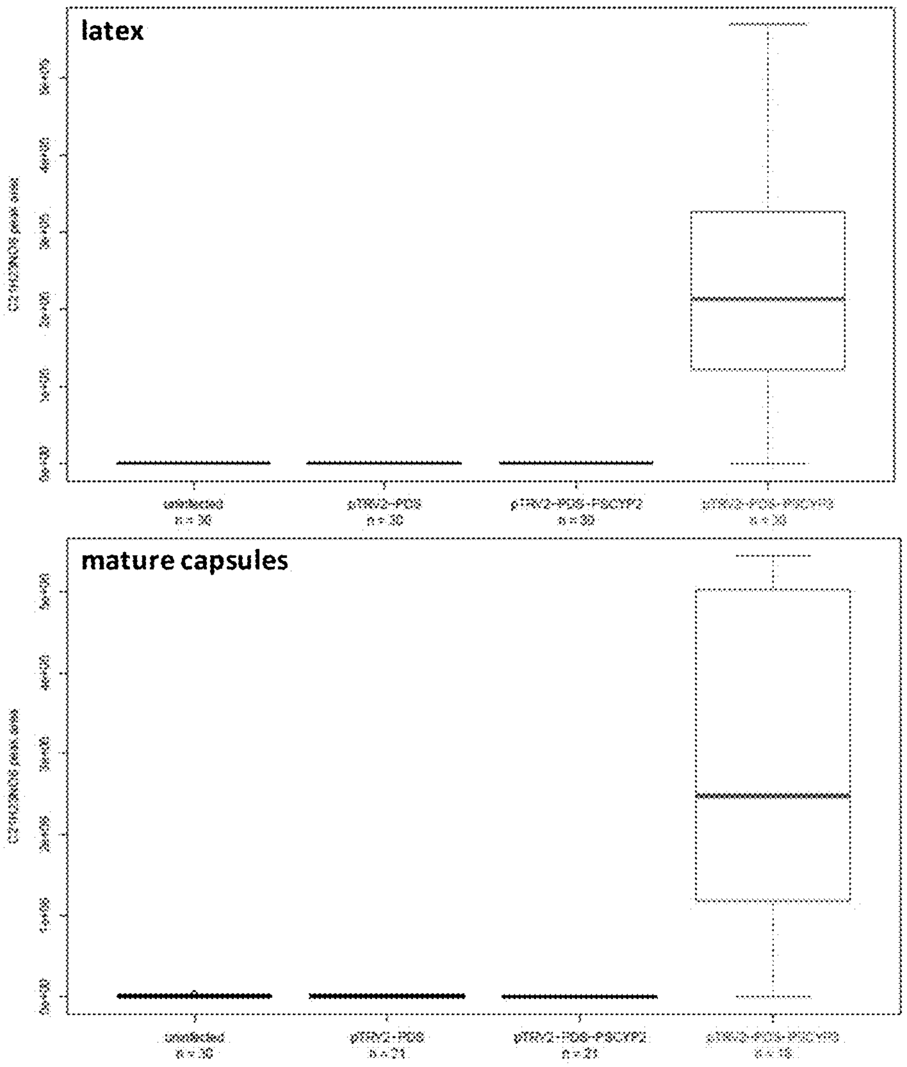
Figure 16:
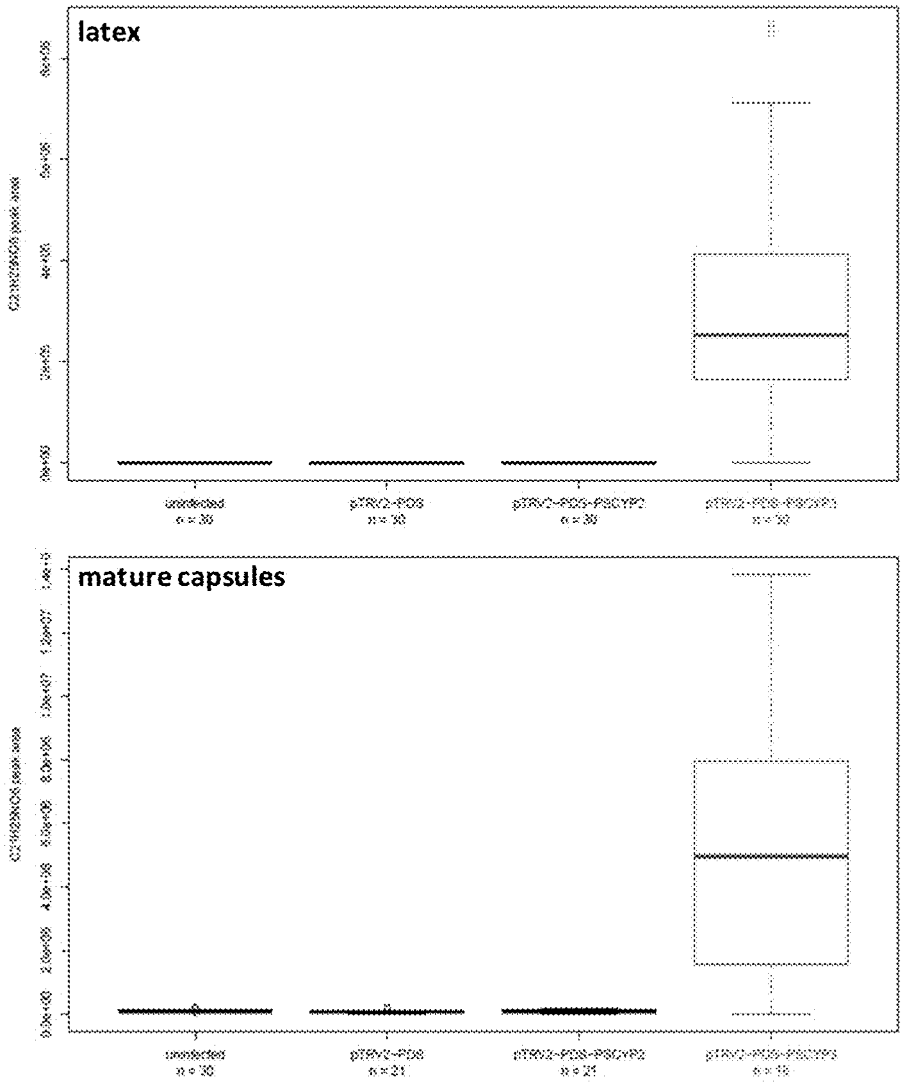

FIG. 8*a* is a tabular representation of the segregation of the PSCYP1 gene in an F2 mapping population derived from a parental cross of cultivars GSK NOSCAPINE CVS1 and GSK THEBAINE CVS1 along with the co-segregation of PSCYP1 and noscapine accumulation in individual F2 plants, FIG. 8*b* is the equivalent representation of the segregation of the PSCYP2 gene, FIG. 8*c* is the equivalent representation of the segregation of the PSCYP3 gene, the PSCYP3 genotyping assay failed on 16 samples (as indicated by the failure to amplify the internal positive control), these samples were excluded from the PSCYP3 co-segregation analysis;

FIG. 9 illustrates a typical UPLC chromatogram for standard solution;

FIG. 10 illustrates a typical UPLC chromatogram for a noscapine containing poppy variety;

FIG. 11 (SEQ ID NO: 12) is the 622 bases long part of the phytoene desaturase gene sequence amplified from cDNA of GSK NOSCAPINE CVS1. The sequence stretch of 129 bases used to silence the phytoene desaturase gene is underlined;

FIG. 12 (SEQ ID NO: 13) is the part of the cDNA sequence used to silence PSCYP2;

FIG. 13 (SEQ ID NO: 14) is the part of the cDNA sequence used to silence PSCYP3;

FIG. 14 shows the normalised peak area of putative tetrahydrocolumbamine in the UPLC chromatograms obtained from latex and mature capsules of plants that displayed the photo-bleaching phenotype after infection with the silencing constructs pTRV2-PDS-PSCYP2, pTRV2-PDS-PSCYP3 or pTRV2-PDS, respectively. The putative tetrahydrocolumbamine peak area obtained from uninfected plants is shown as well;

FIG. 15 shows the normalised peak area of a putative secoberbine alkaloid (in the UPLC chromatograms obtained from latex and mature capsules of plants that displayed the photo-bleaching phenotype after infection with the silencing constructs pTRV2-PDS-PSCYP2, pTRV2-PDS-PSCYP3 or pTRV2-PDS, respectively. The putative secoberbine peak area obtained from uninfected plants is shown as well. The mass, molecular formula and fragmentation pattern of the compound is consistent with demethoxyhydroxymacrantaldehyde or demethoxymacrantoridine; and FIG. 16 shows the normalised peak area of another putative secoberbine alkaloid in the UPLC chromatograms obtained from latex and mature capsules of plants that displayed the photo-bleaching phenotype after infection with the silencing constructs pTRV2-PDS-PSCYP2, pTRV2-PDS-PSCYP3 or pTRV2-PDS, respectively. The putative secoberbine peak area obtained from uninfected plants is shown as well. The mass, molecular formula and fragmentation pattern of the compound is consistent with either demethoxynarcotinediol or narctololinol.

MATERIALS AND METHODS

Generation of EST Libraries a) RNA Isolation and cDNA Synthesis

Material was harvested from stems and capsules at two developmental stages from four poppy cultivars. RNA was prepared individually from five plants per cultivar, developmental stage and organ. The harvested material was ground in liquid nitrogen using a mortar and pestle. RNA was isolated from the ground stem or capsule preparations using a CTAB (hexadecyltrimethylammonium bromide) based method as described in Chang et al. (1993) Plant Molecular Rep. 11: 113-116 with slight modifications (three extractions with chloroform:isoamylalcohol, RNA precipitation with Lithium chloride at −20° C. over night). RNA was quantified spectrophotometrically before pooling equal amounts of RNA from five plants per cultivar, stage and organ. The pooled samples underwent a final purification step using an RNeasy Plus MicroKit (Qiagen, Crawley, UK) to remove any remaining genomic DNA from the preparations. RNA was typically eluted in 30-100 μl water. cDNA was prepared using a SMART cDNA Library Construction Kit (Clontech, Saint-Germainen-Laye, France) according to the manufacturer's instructions but using SuperScript II Reverse Transcriptase (Invitrogen, Paisley, UK) for first strand synthesis. The CDSIII PCR primer was modified to: 5' ATT CTA GAT CCR ACA TGT TTT TTT TTT TTT TTT TTT TVN 3' (SEQ ID NO: 56) where R=A or G, V=A, C or G; N=NT or C/G. cDNA was digested with MmeI (New England Biolabs Inc., Hitchin, UK) followed by a final purification using a QIAquick PCR Purification kit (Qiagen, Crawley, UK).

b) cDNA Pyrosequencing

The Roche 454 GS-FLX sequencing platform (Branford, Conn., USA) was used to perform pyrosequencing on cDNA samples prepared from the following materials for each of the four *P. somniferum* cultivars—GSK MORPHINE CVS1, GSK MORPHINE CVS2, GSK NOSCAPINE CVS1 and GSK THEBAINE CVS1.

1. Stem, 1-3 days after petal fall (early harvest)
2. Stem, 4-6 days after petal fall (late harvest)
3. Capsule, 1-3 days after petal fall (early harvest)
4. Capsule, 4-6 days after petal fall (late harvest)

c) Raw Sequence Analysis, Contiguous Sequence Assembly and Annotation

The raw sequence datasets were derived from parallel tagged sequencing on the 454 sequencing platform (Meyer et al. (2008) Nature Protocols 3: 267-278). Primer and tag sequences were first removed from all individual sequence reads. Contiguous sequence assembly was only performed on sequences longer than 40 nucleotides and containing less than 3% unknown (N) residues. These high quality EST sequences were assembled into unique contiguous sequences with the CAP3 Sequence Assembly Program (Huang and Madan (1999) Genome Research 9: 868-877), and the resulting contigs were annotated locally using the BLAST2 program (Altschul et al.(1997) Nucleic Acids Res. 25: 3389-3402) against the non-redundant peptide database downloaded from the NCBI.

d) Expression Profiling of the Cytochrome P450 Genes

The number of ESTs associated with the respective cytochrome P450 gene consensus sequences were counted in each of the 16 EST libraries. The values obtained were normalised on the basis of the total number of ESTs obtained per library.

Amplification and Sequencing of the Cytochrome P450 Genes from GSK NOSCAPINE CVS1 Genomic DNA.

a) Genomic DNA Preparation

DNA preparation: Leaf samples (30-50 mg) for DNA extraction were harvested from plants of GSK MORPHINE CVS1, GSK MORPHINE CVS2 GSK NOSCAPINE CVS1, GSK THEBAINE CVS1 grown in the glasshouse. DNA was extracted using Qiagen BioSprint 96. Extracted DNA was quantified using Hoescht 33258 and normalized to 10 ng/ul.

b) Amplification and sequencing of the cytochrome P450 genes from DNA of GSK NOSCAPINE CVS1 Primers and primer combinations used for amplification of the respective cytochrome P450 genes from the extracted genomic DNA are shown in Table

TABLE 1

Sequences of forward and reverse primers used to amplify the cytochrome P450 genes from genomic or cDNA

| cytochrome P450 gene | Primer name | Oligonucleotide sequences (5'- to 3'-) (SEQ ID NO:) |
|---|---|---|
| PSCYP1 | PSCYP1_F1 | CTTGAGTCATGCCTTGAT ATGC (15) |
| | PSCYP1_F2 | TTGATGAACGACAAGGAA CCG (16) |
| | PSCYP1_F3 | GCTACGAAAGATAATGGT GCAGC (17) |
| | PSCYP1_F4 | TCGACAGCGCTTACGAAC G (18) |
| | PSCYP1_F8 | GAACCATTAAACACTTGA GTCATGC (19) |
| | PSCYP1_LA_R1 | GCATTTGGTGCTTTCTTC CTCTTCTTTTTCTTATCA GTA (20) |
| | PSCYP1_R1 | AGCAAACCATTCGTCCAT CC (21) |
| | PSCYP1_R3 | TGCAATTGAATTTAGCTC ATCT (22) |
| | PSCYP1_R5 | ATTCATGATTGTGACCTT TGTAATCC (23) |
| | PSCYP1_R7 | TACGACAGGTTGCTAGCT TGG (24) |
| PSCYP2 | PSCYP2_F1 | CAAAGAGTCAATCTGACT CAAGCTAGC (25) |
| | PSCYP2_F2 | TGAAATGCCTGAGATCAC TAAAATCG (26) |
| | PSCYP2_F3 | TCAAACCCTGCTACTAAC ACTTACTTGC (27) |
| | PSCYP2_F4 | TGTAAAGACACTTCATTG ATGGGC (28) |
| | PSCYP2_R1 | GAGATGATCAAGTGGTTT AACCATTCC (29) |
| | PSCYP2_R2 | CGAGTGCCCATGCAGTGG (30) |
| | PSCYP2_R3 | CACTCCATCAGACACACA AGACC (31) |
| | PSCYP2_R4 | GTAAACATTAATGATATT TGGAAGTTTAGATC (32) |
| | PSCYP2_R5 | TTCGATTTGTGTAAACAT TAATGATATTTGG (33) |
| PSCYP3 | PSCYP3_F1 | GTTATCTTTGTCAAATGA ATCCGTTGG (34) |
| | PSCYP3_F2 | AATAATGGATCAGTCACG GCTTCC (35) |

TABLE 1-continued

Sequences of forward and reverse primers used to amplify the cytochrome P450 genes from genomic or cDNA

| cytochrome P450 gene | Primer name | Oligonucleotide sequences (5'- to 3'-) (SEQ ID NO:) |
|---|---|---|
| | PSCYP3_F3 | ATGTGGAAAACGGTAAGC AAGTGG (36) |
| | PSCYP3_F4 | AATCCATCAGATTTTCAA CCAGAGAGG (37) |
| | PSCYP3_R1 | ACGATTCTGTCATCATCA TTTTCGC (38) |
| | PSCYP3_R2 | AGTCGTGTATCGTTCGCT TAATGC (39) |
| | PSCYP3_LA_F2 | GGCTTCCCGGAGATGACC CAGATTTTAT (40) |
| | PSCYP3_LA_F3 | TTGTTATTTTCATGACTA TTACCACCAGCTTCCTCT TA (41) |
| | PSCYP3_LA_F4 | AGTGGAGGAGGCACAAAA GTTAGGATGGAC (42) |
| | PSCYP3_LA_F5 | CCATGTCTGATAAATACG GGTCGGTGTTC (43) |
| | PSCYP3_LA_F6 | TTGTTGATAAGGACGACT AAGAATAAGCAGAAGATA (44) |
| | PSCYP3_LA_R1 | CATGCCTATCTATTTCCT CCCTTGCCCTC (45) |
| | PSCYP3_LA_R2 | TGTCAGCCAACCATTCGT CCATCCTAAC (46) |
| | PSCYP3_LA_R3 | TGTTCGATCACGTTGTCT CTTTTTGCCATAA (47) |
| | PSCYP3_LA_R4 | TAACAATAAAAGTACTGA TAATGGTGGTCGAAGGAG AA (48) |
| | PSCYP3_LA_R5 | ATAATGGTGGTCGAAGGA GAATCAGTAATC(49) |

Primers were designed based on the respective cytochrome P450 contigs assembled from ESTs unique to cultivar GSK NOSCAPINE CVS1. The PSCYP1 and PSCY P2 contigs contained the complete open reading frame of as well as 5' and 3' untranslated regions. PSCYP3 was represented by two contigs covering the 5'- and 3'-ends of the open reading frame with 200 bases from the centre of the open reading frame missing. This missing stretch of coding sequence was amplified and confirmed by amplification and sequencing from cDNA (prepared as described above) in addition to genomic DNA to determine the precise position and of intron 1 (FIG. 3*c*). Amplification were performed on pools of DNA comprising the DNA of at least four individuals and the primer combinations shown in Table 2.

TABLE 2

Primer combinations used to amplify and Sanger-sequence the cytochrome P450 genes from genomic DNA

| cytochrome P450 gene | Primer combination | Annealing temperature [° C.] | Extension time [s] | Sequencing primers used for Sanger sequencing of purified PCR product |
|---|---|---|---|---|
| PSCYP1 | PSCYP1_F8/R3 | 68.5 | 60 | PSCYP1_F3, PSCYP1_F8, PSCYP1_R3 |
| | PSCYP1_F2/R5 | 69.3 | 60 | PSCYP1_F2, PSCYP1_F4, PSCYP1_F5, PSCYP1_R2, PSCYP1_R4, PSCYP1_R5 |
| | PSCYP1_F4/R7 | 69.8 | 60 | PSCYP1_F4, PSCYP1_F6, PSCYP1_R4, PSCYP1_R7 |
| PSCYP2 | PSCYP2_F1/R5 | 61.7 | 60 | PSCYP2_F1, PSCYP2_F2, PSCYP2_F3, PSCYP2_F4, PSCYP2_R1, PSCYP2_R2, PSCYP2_R5 |
| PSCYP3 | PSCYP3_F2/R1 | 66 | 60 | PSCYP3_F2, PSCYP3_F4, PSCYP3_R1, PSCYP3_R2 |
| | PSCYP1_LA_R1/ PSCYP_LA_R1 | See Long Amp PCR | See Long Amp PCR | PSCYP3_LA_F2, PSCYP3_ LA_F3, PSCYP3_ LA_F4, PSCYP3_ LA_F5, PSCYP3_ LA_F6, PSCYP3_LA_R1, PSCYP3_ LA_R2, PSCYP3_ LA_R3, PSCYP3_ LA_R4, PSCYP3_ LA_R5 |

The PCR conditions were as follows:

Reaction Mixture:

| | |
|---|---|
| 5 × HF buffer (Finnzymes) | 5 µl |
| dNTPs (20 mM each) | 0.25 µl |
| Fwd primer (10 µM) | 2.5 µl |
| Rev primer (10 µM) | 2.5 µl |
| DNA (10 ng/µl) | 5 µl |
| Phusion Hot Start (Finnzymes) | 0.25 µl |
| $dH_2O$ | 9.5 µl |
| Reaction volume: | 25 µl |

Phusion Hot Start from Finnzymes was purchased through New England Biolabs, (Bishops Stortford, UK).

PCR Program:

| | | | |
|---|---|---|---|
| | initial denaturation | 98° C. | 1 min |
| 30 cycles of: | denaturation | 98° C. | 30 sec |
| | annealing temperature | Table 2&3 | 30 sec |
| | extension | 72° C. | 40 sec |
| | final extension | 72° C. | 10 min |
| | incubation | 4° C. | storage |

The 5'-end and part of the promoter region of PSCYP3 was amplified from genomic DNA via a long range PCR set up using primers PSCYP1_LA_R1 and PSCYP3_LA_R1:

Long Range PCR Reaction Mixture:

| | |
|---|---|
| 5 × LongAmp buffer (New England Biolabs) | 10 µl |
| dNTPs (10 mM each) | 1.5 µl |
| Fwd primer (10 µM) | 2 µl |
| Rev primer (10 µM) | 2 µl |
| gDNA (100 ng/µl) | 2 µl |
| LongAmp Taq (New England Biolabs) | 2 µl |
| $dH_2O$ | 30.5 µl |
| Reaction volume: | 50 µl |

Long Range PCR Program:

| | | | |
|---|---|---|---|
| | initial denaturation | 94° C. | 30 sec |
| 30 cycles of: | denaturation | 94° C. | 30 sec |
| | annealing & extension | 65° C. | 13.5 min |
| | final extension | 65° C. | 10 min |
| | incubation | 4° C. | storage |

-continued

The products resulting from the various PCRs were purified using the Agencourt AMPure purification kit (Beckman Coulter LTD, Bromley, UK). 30-50 ng of the respective purified PCR products were subjected to Sanger-sequencing using the primers shown in Table 2 as sequencing primers. Since primer combination PSCYP1_F4/R7 resulted in amplification of a smaller, unspecific product in addition to the expected amplicon (see also FIG. 4*d*), the latter was excised and purified from the gel using QIAEX II Gel Extraction Kit (Qiagen, Hilden, Germany) prior to sequencing.

The amino acid sequences of the respective cytochrome P450s, predicted from the Sanger-sequence confirmed open reading frame sequences, were compared to protein sequences deposited in the non-redundant protein database using the Standard Protein BLAST program (blastp).

c) Analysis of genomic DNA from GSK MORPHINE CVS1, GSK MORPHINE CVS2, GSK NOSCAPINE CVS1 and GSK THEBAINE CVS1 for the presence of cytochrome P450 genes To investigate if the cytochrome P450 genes were present in all four cultivars, amplification from genomic DNA (pools of four individuals per cultivar) of GSK MORPHINE CVS1, GSK MORPHINE CVS2, GSK NOSCAPINE CVS1 and GSK THEBAINE CVS1 was performed in a series of overlapping fragments using primer combinations shown in Table 3. Exactly the same PCR conditions as described above to obtain the full length genomic sequences from GSK NOSCAPINE CVS1 were used. =0.5 µl of each PCR reaction was resolved on 1% agarose alongside an appropriate size standards.

TABLE 3

Primer combinations used to amplify the cytochrome P450 genes from genomic DNA

| cytochrome P450 gene | Primer combination | Annealing temperature [° C.] | Extension time [s] | Expected fragment size [bp] | IG. |
|---|---|---|---|---|---|
| PSCYP1 | PSCYP1__F1/R3 | 66 | 40 | 1051 | FIG. 5a |
| | PSCYP1__F8/R3 | 68.5 | 60 | 1064 | FIG. 5b |

TABLE 3-continued

| Primer combinations used to amplify the cytochrome P450 genes from genomic DNA | | | | | |
|---|---|---|---|---|---|
| cytochrome P450 gene | Primer combination | Annealing temperature [° C.] | Extension time [s] | Expected fragment size [bp] | IG. |
| | PSCYP1_F2/R5 | 69.3 | 60 | 1400 | FIG. 5c |
| | PSCYP1_F4/R7 | 69.8 | 60 | ~1200 | FIG. 5d |
| PSCYP2 | PSCYP2_F1/R1 | 61 | 60 | 596 | FIG. 6a |
| | PSCYP2_F2/R2 | 61 | 60 | 596 | FIG. 6b |
| | PSCYP2_F3/R3 | 61 | 60 | 603 | FIG. 6c |
| | PSCYP2_F4/R4 | 61 | 60 | 475 | FIG. 6d |
| PSCYP3 | PSCYP3_F1/R1 | 66 | 60 | 994 | FIG. 7a |
| | PSCYP3_F2/R2 | 66 | 60 | 418 | FIG. 7b |
| | PSCYP3_F3/R2 | 66 | 60 | 122 | FIG. 7c |
| | PSCYP3_F3/R1 | 66 | 60 | 638 | FIG. 7d |

Generation of a Mapping Population, Extraction and Analysis of Genomic DNA from Leaf Material Plus Extraction and Analysis of Alkaloids from Poppy Straw a) DNA Extraction from F2 Plants 40-50 mg of leaf tissue was harvested, in duplicate, from all poppy plants within the GSK NOSCAPINE CVS1×GSK THEBAINE CVS1 F2 mapping population and parental plants) at the 'small rosette' growth stage (~10 leaves present on each plant).

Leaf tissue (40-50 mg wet weight) was collected into 1.2 ml sample tubes in 8×12 format (Part Number 1760-00, Scientific Specialties Inc, 130 Thurman St, Lodi, Calif. 95240 USA), closed with strip caps (Part Number 1702-00, Scientific Specialties Inc) and shipped to the AGRF (Australian Genome Research Facility) Adelaide on Techni-Ice dry Ice packs by overnight courier.

On receipt, strip caps were removed and a 3 mm tungsten carbide bead was added to each tube (Part Number 69997, Qiagen GmbH, Hilden, Germany). Samples were placed at −80° C. (Freezer model; Sanyo MDF-U73V) for a minimum of two hours prior to freeze-drying for 18 hr (Christ Model Alpha 2-4 LSC).

Following freeze drying, tubes were sealed with fresh strip caps (as above), and samples were powdered by bead-milling (Model "Tissue Lyser", Part Number 85300; Qiagen) at 3,000 RPM for 2×60 sec cycles separated by plate inversion. DNA extraction was performed using the "Nucleospin Plant II" system (Macherey-Nagel, GmbH & Co. KG Neumann-Neander-Straβe 6-8, 52355 Düren, Germany).

Cell lysis was performed using the supplied Buffer Set PL2/3. The manufacturer's protocol for centrifugal extraction was followed (Centrifuge model 4-K 15; Sigma Laborzentrifugen GmbH, 37520 Osterode am Harz, Germany).

The recovered DNA (12/96 samples, one sample per plate column) was checked for quality and quantity by ultra violet spectroscopy (Model Nanodrop-8000; NanoDrop products, 3411 Silverside Rd, Bancroft Building; Wilmington, Del. 19810, USA) at 230, 260 and 280 nM.

b) Genotyping of F2 DNA Samples for the Presence of Absence of the Cytochrome P450 Genes DNA samples from a total of 275 F2 plants were genotyped for the presence or absence of PSCYP1, PSCYP2 and PSCYP3, respectively, by amplifying a short fragment of each of the genes. In order to fluorescently label the resulting PCR fragments, the forward primers carried a VIC-label (Applied Biosystems, UK) at their 5'-prime ends. Fragment analyses were carried out on the 96-capillary electrophoresis 3730xl DNA Analyzer (Applied Biosystems, UK) according to the manufacturer's instructions. In addition to the respective cytochrome P450 fragments, an internal positive control was amplified in each PCR assay in order to distinguish lack of amplification due to absence of the cytochrome P450 genes in the DNA samples from lack of amplification caused by PCR assay failures. Samples were the PCR assay had failed were excluded from the co-segragation analyses of the genes with the noscapine trait.

The following primers were used (primer sequences are shown in Table 1; forward primers were 5'-end-labeled with VIC):

PSCYP1: VIC-PSCYP1_F3/PSCYP1_R2; amplified fragment size: 166 bp

PSCYP2: VIC-PSCYP2_F2/PSCYP2_R1; amplified fragment size: 226 bp

PSCYP3: VIC-PSCYP3_F3/PSCYP3_R1; amplified fragment size: 638 bp

The PSCYP1-fragment was amplified with the following PCR conditions:

Reaction Mixture:

| | |
|---|---|
| 5 × GoTaq Buffer (Promega) | 2 μl |
| dNTPs (2.5 mM mix) | 0.5 μl |
| $MgCl_2$ (25 mM) | 0.6 μl |
| Forward primer (10 μM) | 0.5 μl |
| Reverse primer (10 μM) | 0.5 μl |
| gDNA (5 ng/μl) | 2 μl |
| GoTaq (Promega) | 0.2 μl |
| $dH_2O$ | 3.7 μl |
| Reaction volume: | 10 μl |

PCR Program:

| | | | |
|---|---|---|---|
| | initial denaturation | 94° C. | 1 min |
| 30 cycles of: | denaturation | 94° C. | 30 sec |
| | annealing temperature | 62° C. | 30 sec |
| | extension | 72° C. | 20-30 sec |
| | final extension | 72° C. | 5 min |
| | incubation | 4° C. | storage |

The PSCYP2- and PSCYP3-fragments were amplified with the following PCR conditions:

Reaction Mixture:

| | |
|---|---|
| 5 × Type-it multiplex PCR mix (Qiagen) | 5 μl |
| Forward primer (10 μM) | 0.5 μl |

-continued

| | |
|---|---|
| Reverse primer (10 μM) | 0.5 μl |
| gDNA (5 ng/μl) | 2 μl |
| $dH_2O$ | 2 μl |
| Reaction volume: | 10 μl |

PCR Program:

| | | | |
|---|---|---|---|
| | initial denaturation | 95° C. | 15 min |
| 30 cycles of: | denaturation | 95° C. | 15 sec |
| | annealing temperature | 60° C. | 30 sec |
| | extension | 72° C. | 30 sec |
| | final extension | 72° C. | 5 min |
| | incubation | 4° C. | storage |

c) Poppy Straw Analysis

Poppy capsules were harvested by hand from the mapping population once capsules had dried to approximately 10% moisture on the plant. The seed was manually separated from the capsule, and capsule straw material (Poppy Straw) was then shipped to the GSK extraction facility in Port Fairy, Australia.

The poppy straw samples were then ground in a Retsch Model MM04 ball mill into a fine powder. Two gram samples of ground poppy straw were then weighed accurately (2±0.003 g) and extracted in 50 mL of a 10% acetic acid solution. The extraction suspension was shaken on an orbital shaker at 200 rpm for a minimum of 10 minutes then filtered to provide a clear filtrate. The final filtrate was passed through a 0.22 μm filter prior to analysis.

The solutions were analysed using a Waters Acquity UPLC system fitted with a Waters Acquity BEH C18 column, 2.1 mm×100 mm with 1.7 micron packing. The mobile phase used a gradient profile with eluent A consisting of 0.1% Trifluoroacetic acid in deionised water and eluent B consisting of 100% Acetonitrile. The mobile phase gradient conditions used are as listed in Table 2, the gradient curve number as determined using a Waters Empower chromatography software package. The flow rate was 0.6 mL per minute and the column maintained at 45 C. The injection volume was 1 μL injection volume and the alkaloids were detected using a UV detector at 285 nm.

The loss on drying (LOD) of the straw was determined by drying in an oven at 105 degrees centrigrade for 3 hours.

Gradient Flow Program

| TIME (minutes) | % Eluent A | % Eluent B | Flow (mL/min) | Curve No |
|---|---|---|---|---|
| 0.00 | 95.0 | 5.0 | 0.60 | INITIAL |
| 0.80 | 90.0 | 10.0 | 0.60 | 6 |
| 3.40 | 75.0 | 25.0 | 0.60 | 3 |
| 3.60 | 95.0 | 5.0 | 0.60 | 6 |
| 4.00 | 95.0 | 5.0 | 0.60 | 11 |

Alkaloid concentrations for morphine, codeine, thebaine, oripavine and noscapine were determined by comparison with standard solutions and the results calculated on a dry weight basis.

Typical retention times are as follows:

| Compound | Retention Time (minutes) |
|---|---|
| Morphine | 1.14 |
| Pseudo morphine | 1.26 |

-continued

| Compound | Retention Time (minutes) |
|---|---|
| Codeine | 1.69 |
| Oripavine | 1.80 |
| 10-Hydroxythebaine | 2.32 |
| Thebaine | 2.53 |
| Noscapine | 3.16 |

Virus Induced Gene Silencing (VIGS) of PSCYP3 and PSCYP3 a) Generation of Silencing Constructs

A tobacco rattle virus (TRV) based virus induced gene silencing system developed and described by Liu et al. (2002) Plant J. 30(4): 415-429 was used to investigate the gene function of PSCYP2 and PSCYP3. DNA fragments selected for silencing of PSCYP2 and PSCYP3, respectively, were amplified by PCR and cloned into the silencing vector pTRV2 (GenBank accession no. AF406991; Liu et al. (2002) Plant J. 30(4): 415-429). They were linked to a 129 bp-long fragment of the *P. somniferum phytoene* desaturase gene (PsPDS) in order to silence the respective cytochrome P450 genes and PsPDS simultaneously. Plants displaying the photo-bleaching phenotype that resulted from silencing of PsPDS (Hileman et al. (2005) Plant J. 44(2): 334-341) were identified as plants successfully infected with the respective silencing constructs and selected for analysis.

Generation of the pTRV2-PDS construct: A 622 bp fragment (FIG. 11) of PsPDS was amplified from cDNA prepared from GSK NOSCAPINE CVS1 as described above using primers ps_pds_F and ps_pds_R4 (Table 4).

TABLE 4

Primers used to amplify sequences selected for virus induced gene silencing

| Target gene to be silenced | Primer name | Oligonucleotide sequences (5'- to 3'-) (SEQ ID NO:) (in capitals: gene-specific sequence; in lower case: added sequence; underlined: restriction sites) |
|---|---|---|
| PS PHYTOENE DESATURASE | ps_pds_F | GAGGTGTTCATTGCCATGTCAA (50) |
| | ps_pds_R4 | GTTTCGCAAGCTCCTGCATAGT (51) |
| PSCYP2 | VIGS_PSCYP2_F | aaactcgagaagcttATGATCATGAGTAACTTATGGA (52) |
| | VIGS_PSCYP2_R | aaaggtaccCCAACAGGCCATTCCGTTG (53) |
| PSCYP3 | VIGS_PSCYP3_F | aaactcgagaagcttTAGGAGGGTATGTCCGGC (54) |
| | VIGS_PSCYP3_R | aaaggtaccTTAACTCCGCCTCGGCTCC (55) |

The sequence of the forward primer was based on a 412 bp long contig derived from the EST-libraries which shared 99% identity at its 3' end with the partial coding sequence of the *P. somniferum* phytoene desaturase (GenBank accession no. DQ116056). The sequence of the reverse primer was designed based on the DQ116056 sequence. The PCR conditions were identical to those described above for the amplification of the cytochrome P450 genes from genomic sequence except that the annealing step was carried out at 70° C. and the extension time was increased to 60 seconds.

Sau3AI digestion of the PCR-fragment yielded among others two fragments (280 bp and 129 bp in length) that carried BamHI-compatible sticky ends at both, their 5' and 3' ends. The 129 bp long fragment (underlined stretch in FIG. 11) was cloned into the BamHI site of the pTRV2 vector. Because Sau3AI was used to produce BamHI-compatible sticky ends, the BamHI site at the 5-end of the PDS-insert was abolished in the pYL156-PDS construct. However, the BamHI recognition site at its 3'-end was kept intact due to the nature of the PDS-insert sequence.

A sequence-confirmed pTRV2-PDS construct, with the 129 bp fragment in sense orientation, was subsequently used as a vector for generating the PSCYP2 and PSCYP3 silencing constructs, and served as a control in the VIGS experiments.

Generation of silencing constructs for PSCYP2 and PSCYP3 (pTRV2-PDS-PSCYP2 and pTRV2-PDS-PSCYP3): The DNA fragments selected for silencing PSCYP2 and PSCYP3 were amplified from cDNA of GSK NOSCAPINE CVS1 prepared as described above with the use of the primer sequences shown in Table 4. Additional restriction sites (forward primers: XhoI and HindIII for forward primers; KpnI site for reverse primers) were added to the gene-specific primers in order to facilitate cloning. The amplification conditions were as described above for amplifying the PDS-fragment except that the annealing temperatures were 60.9° C. for PSCYP2 and 66° C. for PSCYP3 and the extension time was 30 seconds.

The sequence selected to silence PSCYP2 (FIG. 12) and PSCYP3 (FIG. 12), respectively, were cloned into pTV00 (Ratcliff et al. (2001) Plant J. 25(2): 237-245) using HindIII and KpnI and subcloned into pTRV2-PDS using BamHI and KpnI. Sequence-confirmed pTRV2-PDS-PSCYP2 and pTRV2-PDS-PSCYP3 constructs were used in the VIGS experiments.

b) Transformation of Constructs into *Agrobacterium Tumefaciens*

The propagation of the silencing constructs was carried out with the *E. coli* strain DH5a and, subsequently, the respective silencing constructs, as well as pTRV1 (GenBank accession no. AF406990; Liu et al. (2002) Plant J. 30(4): 415-429) were independently transformed into electrocompetent *Agrobacterium tumefaciens* (strain GV3101).

c) Infiltration of Plants

Overnight liquid cultures of *A. tumefaciens* containing each silencing construct were used to inoculate Luria-Bertani (LB) medium containing 10 mM MES, 20 μM acetosyringone and 50 μg/ml kanamycin. Cultures were maintained at 28° C. for 24 hours, harvested by centrifugation at 3000 g for 20 min, and resuspended in infiltration solution (10 mM MES, 200 μM acetosyringone, 10 mM MgCl2) to an OD600 of 2.5. *A. tumefaciens* harbouring the respective constructs (pTRV2-PDS-PSCYP2, pTRV2-PDS-PSCYP3 or, as a control, pTRV2-PDS) were each mixed 1:1 (v/v) with *A. tumefaciens* containing pTRV1, and incubated for two hours at 22° C. prior to infiltration. Two weeks old seedlings of GSK NOSCAPINE CVS1 grown under standard greenhouse conditions (22° C., 16 h photoperiod), with emerging first leaves, were infiltrated as described by Hagel and Facchini (2010) Nat. Chem. Biol. 6: 273-275.

d) Latex and Capsule Analysis of Silenced Plants

Leaf latex of infiltrated opium poppy plants displaying photo-bleaching as a visual marker for successful infection and silencing was analysed when the first flower buds emerged (~7 week old plants). Plants showing a similar degree of photo-bleaching of leaves were selected for analysis.

Latex was collected from cut petioles, with a single drop dispersed into 500 μL 10% acetic acid. This was diluted 10× in 1% acetic acid to give an alkaloid solution in 2% acetic acid for further analysis. Capsules were harvested by hand from glasshouse-grown from the same plants used for latex analysis and single capsules were ground in a Retsch Model MM04 ball mill into a fine powder. Ten mg samples of ground poppy straw were then weighed accurately (10±0.1 mg) and extracted in 0.5 mL of a 10% acetic acid solution with gentle shaking for 1 h at room temperature. Samples were then clarified by centrifugation and a 50 μL subsample diluted 10× in 1% acetic acid to give an alkaloid solution in 2% acetic acid for further analysis.

All solutions were analysed using a Waters Acquity UPLC system fitted with a Waters Acquity BEH C18 column, 2.1 mm×100 mm with 1.7 micron packing. The mobile phase used a gradient profile with eluent A consisting of 10 mM ammonium bicarbonate pH 10.2 and eluent B methanol. The mobile phase gradient conditions used are as listed in Table 1, with a linear gradient. The flow rate was 0.5 mL per minute and the column maintained at 60° C. The injection volume was 2 μL and eluted peaks were ionised in positive APCI mode and detected within ~3 ppm mass accuracy using a Thermo LTQ-Orbitrap. The runs were controlled by Thermo Xcalibur software.

—Gradient Flow Program:

| TIME (minutes) | % Eluent A | % Eluent B | Flow (mL/min) |
|---|---|---|---|
| 0.0 | 98.0 | 2.0 | 0.50 |
| 0.2 | 98.0 | 2.0 | 0.50 |
| 0.5 | 60.0 | 40 | 0.50 |
| 4.0 | 20.0 | 80.0 | 0.50 |
| 4.5 | 20.0 | 0.0 | 0.50 |

All data analysis was carried out in R. Putative alkaloid peaks were quantified by their pseudomolecular ion areas using custom scripts. Peak lists were compiled and any peak-wise significant differences between samples were identified using 1-way ANOVA with p-values adjusted using the Bonferroni correction for the number of unique peaks in the data set. For any peak-wise comparisons with adjusted p-values<0.05, Tukey's HSD test was used to identify peaks that were significantly different between any given sample and the control. Alkaloids were identified by comparing exact mass and retention time values to those of standards. Where standards were not available, neutral exact masses were used to generate molecular formulae hits within elemental constraints of C=1:100, H=1:200, O=0:200, N=0:3 and mass accuracy<20 ppm. The hit with the lowest ppm error within these constraints was used to assign a putative formula.

Example 1

Assembly of Full Length PSCYP1 cDNA Sequence from ESTs and Confirmation by Sequencing from Genomic DNA.

The full length open reading frame of PSCYP1 (FIG. 1*a*) was assembled from ESTs derived from the 454 sequencing platform using the CAP3 sequence assembly programme. The full length cDNA sequence was confirmed by direct amplification of the full length cDNA from GSK NOSCAPINE CVS1 genomic DNA.

Example 2

PSCYP1 is Exclusively Expressed in the Noscapine Producing *Papaver somniferum* Cultivar GSK Noscapine CVS1.

Figure 2A:
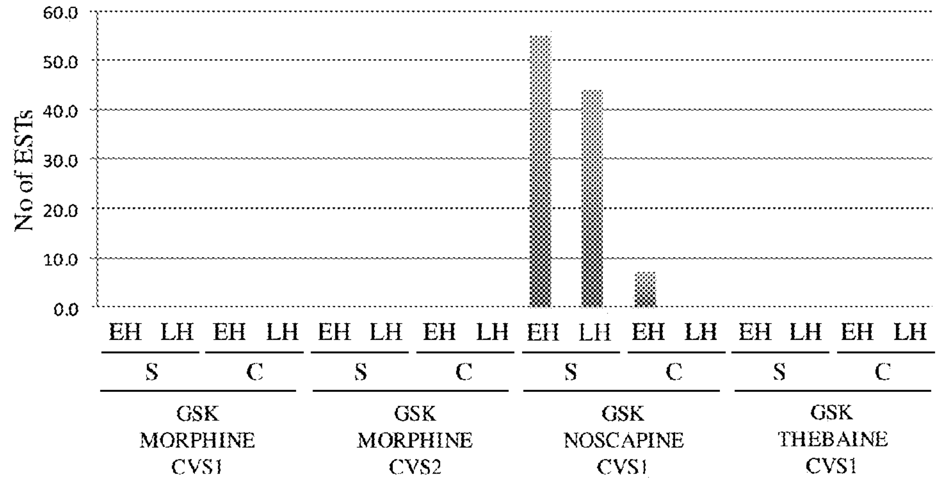

FIG. 2*a* shows the normalized distribution of ESTs associated with the PSCYP1 consensus sequence across each of the 16 EST libraries prepared from two organs (capsules and stems) at two developmental stages (early and late harvest) from each of the four poppy cultivars, GSK MORPHINE CVS1, GSK MORPHINE CVS2, GSK NOSCAPINE CVS1 and GSK THEBAINE CVS1. ESTs corresponding to PSCYP1 were exclusively found in libraries derived from the noscapine producing cultivar GSK NOSCAPINE CVS1 (FIG. 2*a*). PSCYP1 expression was strongest in stem tissue shortly after flowering.

Example 3

PCR-Amplification of PSCYP1 from Genomic DNA of the Four *Papaver somniferum* Cultivars GSK Morphine CVS1, GSK Morphine CVS2, GSK Noscapine CVS1 and GSK Thebaine CVS1.

PCR-amplifications of PSCYP1 fragments were performed on genomic DNA from the four poppy cultivars GSK MORPHINE CVS1, GSK MORPHINE CVS2, GSK NOSCAPINE CVS1 and GSK THEBAINE CVS1 using the primer combinations shown in Table 2 and 3.

Figure 5:
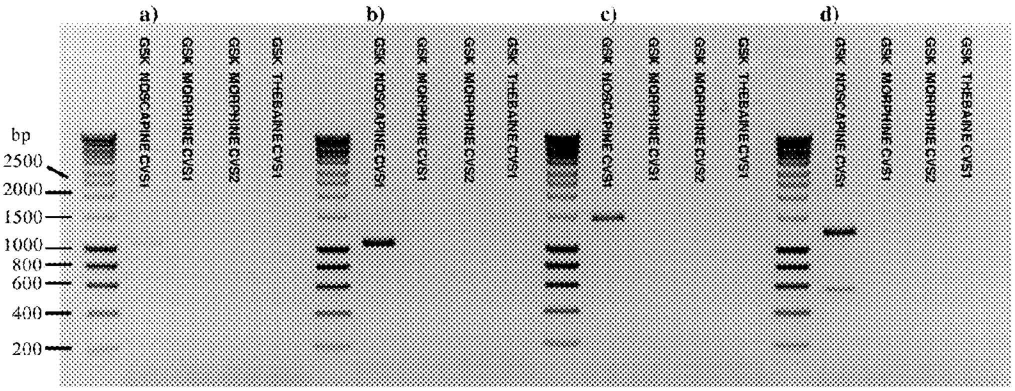
FIG. 5 illustrates that the PSCYP1 gene sequence is only present in cultivar GSK NOSCAPINE CVS1 and is absent from cultivars GSK MORPHINE CVS1, GSK MORPHINE CVS2 and GSK THEBAINE CVS1.

FIG. 5 shows the PCR-amplification of PSCYP1 from genomic DNA of the four *Papaver somniferum* cultivars GSK MORPHINE CVS1, GSK MORPHINE CVS2, GSK NOSCAPINE CVS1 and GSK THEBAINE CVS1;

The amplification from genomic DNA yielded the gene sequence shown in FIG. 3*a*.

Example 4

The Putative Protein Encoded by PSCYP1 Shows Highest Sequence Similarity to a Cytochrome P450 from *Coptis japonica* and *Thalictrum flavum*.

The closest homologues to the putative protein encoded by the PSCYP1 open reading frame (FIG. 4*a*) are a cytochrome P450 from *Coptis japonica* (GenBank accession no. BAF98472.1, 46% identical at amino acid level). The closest homologue with an assignment to a cytochrome P450 subfamily is CYP82C4 from *Arabidopsis lyrata* (GenBank accession no. XP_002869304.1, 44% identical at amino acid level).

Example 5

PSCYP1 is Only Present in the Genome of the Noscapine Producing *P. Somniferum* Cultivar GSK NOSCAPINE CVS1.

The transcribed region covered by the ESTs contained the complete coding sequence of PSCYP1 (including 5' and 3' untranslated regions), which was used for primer design (Table 1) to amplify the PSCYP1 gene from genomic DNA in a series of overlapping fragments for sequencing. Upon testing a subset of the primer combinations (Table 3) on genomic DNA samples from all four cultivars it was discovered that the PSCYP1 fragments could only be amplified from genomic DNA of the noscapine producing cultivar GSK NOSCAPINE CVS1 but not from genomic DNA of the predominantly morphine (GSK MORPHINE CVS1, GSK MORPHINE) or thebaine (GSK THEBAINE CVS1) producing cultivars (FIG. 5). The PCR amplifications were performed on pools of genomic DNA comprising DNA from four individuals per cultivar. This discovery explains why the PSCYP1 is only expressed in the GSK NOSCAPINE CVS1 cultivar and is absent from the transcriptome of the other three cultivars.

Example 6

Assembly of Full Length PSCYP2 cDNA Sequence from ESTs and Confirmation by Sequencing from Genomic DNA.

The full length open reading frame of PSCYP2 (FIG. 1*b*) was assembled from ESTs derived from the 454 sequencing platform using the CAP3 sequence assembly programme. The full length cDNA sequence was confirmed by direct amplification of the full length cDNA from GSK NOSCAPINE CVS1 genomic DNA.

Example 7

PSCYP2 is Exclusively Expressed in the Noscapine Producing *Papaver somniferum* Cultivar GSK NOSCAPINE CVS1.

Figure 2B:
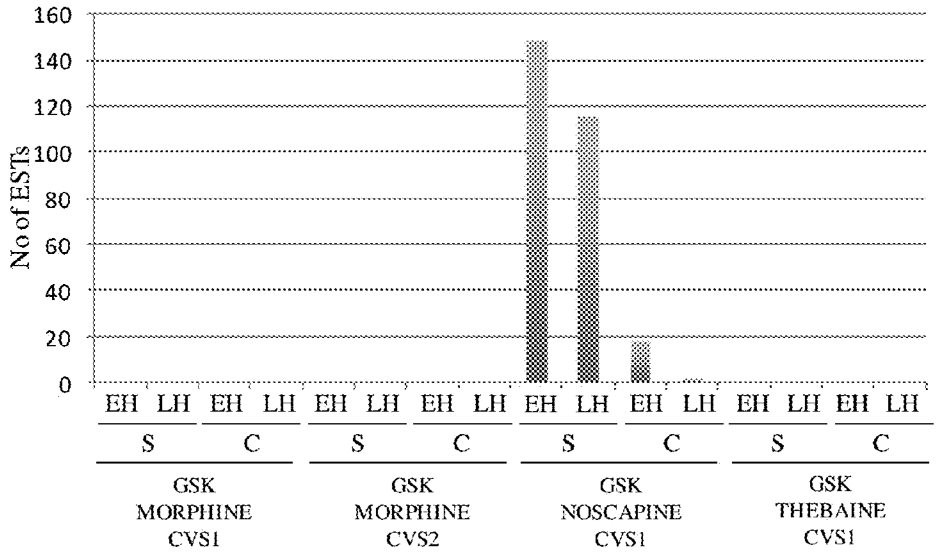

FIG. 2*b* shows the normalized distribution of ESTs associated with the PSCYP2 consensus sequence across each of the 16 EST libraries prepared from two organs (capsules and stems) at two developmental stages (early and late harvest) from each of the four poppy cultivars, GSK MORPHINE CVS1, GSK MORPHINE CVS2, GSK NOSCAPINE CVS1 and GSK THEBAINE CVS1. ESTs corresponding to PSCYP2 were exclusively found in libraries derived from the noscapine producing cultivar GSK NOSCAPINE CVS1 (FIG. 2*b*). PSCYP2 expression was strongest in stem tissue shortly after flowering.

Example 8

PCR-Amplification of PSCYP2 from Genomic DNA of the Four *Papaver somniferum* Cultivars GSK Morphine CVS1, GSK Morphine CVS2, GSK Noscapine CVS1 and GSK Thebaine CVS1.

Figure 6:
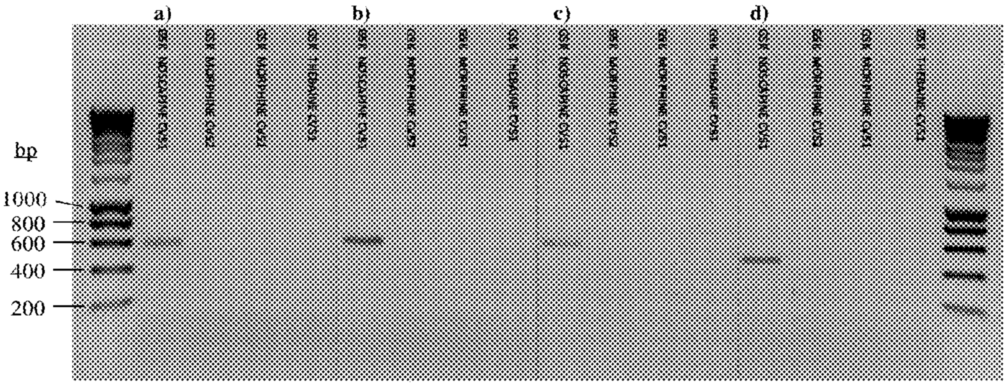
FIG. 6 illustrates that the PSCYP2 gene sequence is only present in cultivar GSK NOSCAPINE CVS1 and is absent from cultivars GSK MORPHINE CVS1, GSK MORPHINE CVS2 and GSK THEBAINE CVS1.

PCR-amplifications of PSCYP2 fragments were performed on genomic DNA from the four poppy cultivars GSK MORPHINE CVS1, GSK MORPHINE CVS2, GSK NOSCAPINE CVS1 and GSK THEBAINE CVS1 using the primer combinations shown in Table 2 and 3. FIG. 6 shows the PCR-amplification of PsCYP2 from genomic DNA of the four *Papaver somniferum* cultivars GSK MORPHINE CVS1, GSK MORPHINE CVS2, GSK NOSCAPINE CVS1 and GSK THEBAINE CVS1;

The amplification from genomic DNA yielded the gene sequence shown in FIG. 3*b*.

Example 9

The Putative Protein Encoded by PSCYP2 Shows Highest Sequence Similarity to a Cytochrome P450 from *Coptis japonica* and *Thalictrum flavum*.

The closest homologues to the putative protein encoded by the PSCYP2 open reading frame (FIG. 4*b*) are cytochrome P450s annotated as stylopine synthase from *Argemone mexicana* (GenBank accession no. ABR14721, identities: 366/475 (78%)) and from *Papaver somniferum* (GenBank accession no. ADB89214, identities=373/491 (76%)). The sequence comparisons were carried out using NCBI's 'blastp' algorithm (method: compositional matrix adjust).

Example 10

PSCYP2 is Only Present in the Genome of the Noscapine Producing *P. Somniferum* Cultivar GSK Noscapine CVS1.

The transcribed region covered by the ESTs contained the complete coding sequence of PSCYP2 (including 5' and 3' untranslated regions), which was used for primer design (Table 1) to amplify the PSCYP2 gene from genomic DNA in a series of overlapping fragments for sequencing. Upon testing a subset of the primer combinations (Table 3) on genomic DNA samples from all four cultivars it was discovered that the PSCYP2 fragments could only be amplified from genomic DNA of the noscapine producing cultivar GSK NOSCAPINE CVS1 but not from genomic DNA of the predominantly morphine (GSK MORPHINE CVS1, GSK MORPHINE) or thebaine (GSK THEBAINE CVS1) producing cultivars (FIG. 6). The PCR amplifications were performed on pools of genomic DNA comprising DNA from four individuals per cultivar. This discovery explains why the PSCYP2 is only expressed in the GSK NOSCAPINE CVS1 cultivar and is absent from the transcriptome of the other three cultivars.

Example 11

Assembly of the Full Length PSCYP3 cDNA Sequence from ESTs and by Sequencing from cDNA and Genomic DNA.

Two possible full length open reading frames of PSCYP3 (FIGS. 1*c* and 1*d*) were partially assembled from ESTs derived from the 454 sequencing platform using the CAP3 sequence assembly programme. The ESTs covered the 5' and 3' area of the sequence with a stretch of 200 bases missing. The missing stretch of bases was obtained by direct amplification and sequencing from cDNA of the GSK NOSCAPINE CVS1. The full length sequences were further confirmed by direct amplification and sequencing of PSCYP3 from genomic DNA of the GSK NOSCAPINE CVS1. Two possible ATG start codons were identified. Since they were in frame and adjacent to each other the resulting full length open reading frame sequences shown in FIGS. 1*c* and 1*d*, respectively, differ only by one ATG codon at the 5'-terminus.

Example 12

PSCYP3 is Exclusively Expressed in the Noscapine Producing *Papaver Somniferum* Cultivar GSK NOSCAPINE CVS1.

Figure 2C:
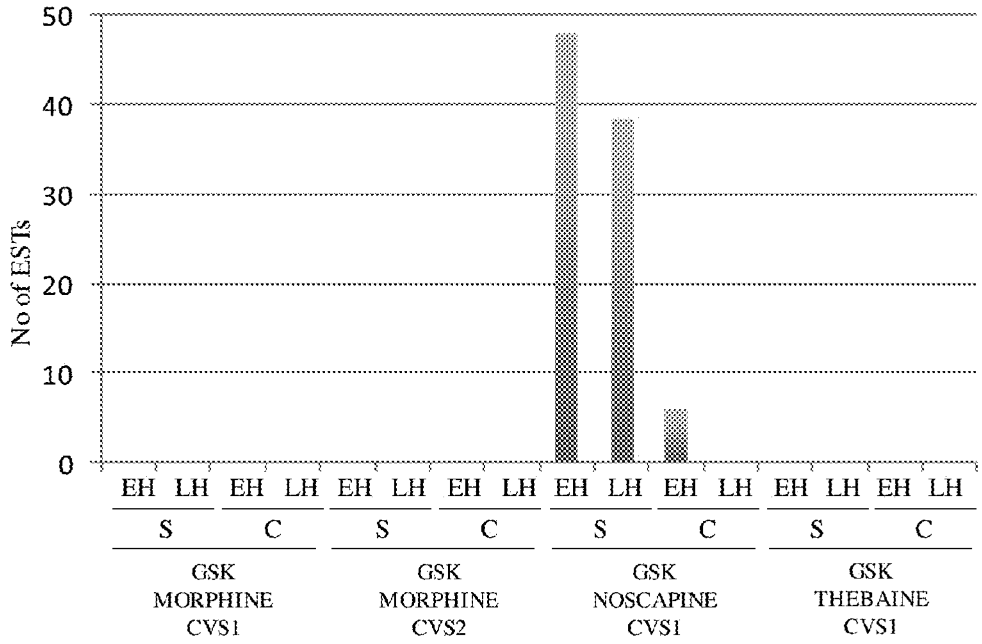

FIG. 2*c* shows the normalized distribution of ESTs associated with the PSCYP3 consensus sequence across each of the 16 EST libraries prepared from two organs (capsules and stems) at two developmental stages (early and late harvest) from each of the four poppy cultivars, GSK MORPHINE CVS1, GSK MORPHINE CVS2, GSK NOSCAPINE CVS1 and GSK THEBAINE CVS1. ESTs corresponding to PSCYP3 were exclusively found in libraries derived from the noscapine producing cultivar GSK NOSCAPINE CVS1 (FIG. 2*c*). PSCYP3 expression was strongest in stem tissue shortly after flowering.

Example 13

PCR-Amplification of PSCYP3 from Genomic DNA of the Four *Papaver Somniferum* Cultivars GSK Morphine CVS1, GSK Morphine CVS2, GSK Noscapine CVS1 and GSK Thebaine CVS1.

Figure 7:
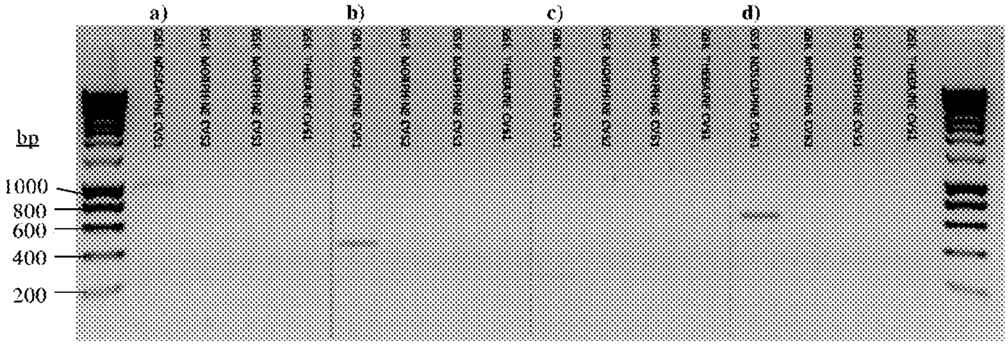
FIG. 7 illustrates that the PSCYP3 gene sequence is only present in cultivar GSK NOSCAPINE CVS1 and is absent from cultivars GSK MORPHINE CVS1, GSK MORPHINE CVS2 and GSK THEBAINE CVS1.

PCR-amplifications of PSCYP3 fragments were performed on genomic DNA from the four poppy cultivars GSK MORPHINE CVS1, GSK MORPHINE CVS2, GSK NOSCAPINE CVS1 and GSK THEBAINE CVS1 using the primer combinations shown in Table 2 and 3. FIG. 7 shows the PCR-amplification of PSCYP3 from genomic DNA of the four *Papaver somniferum* cultivars GSK MORPHINE CVS1, GSK MORPHINE CVS2, GSK NOSCAPINE CVS1 and GSK THEBAINE CVS1;

The amplification from genomic DNA yielded the gene sequence shown in FIG. 3*c*.

Example 14

The Putative Protein Encoded by PSCYP3 Shows Highest Sequence Similarity to Protopine 6-Hydroxylase from *Eschscholzia californica.*

The closest homologue to the putative proteins encoded by the two possible PSCYP3 open reading frames (FIGS. 1*c* and 1*d*) is a cytochrome P450s annotated as protopine 6-hydroxylase from *Eschscholzia californica* (GenBank accession no. BAK20464, identities: 228/522 (44%)) and a cytochrome P450 from *Coptis japonica* (GenBank accession no. BAF98472, identities=230/539 (43%)). The sequence comparisons were carried out using NCBI's 'blastp' algorithm (method: compositional matrix adjust).

Example 15

PSCYP3 is Only Present in the Genome of the Noscapine Producing *P. Somniferum* Cultivar GSK Noscapine CVS1.

The transcribed region covered by the ESTs contained the partial coding sequence of PSCYP3 (including 5' and 3' untranslated regions), which was used for primer design (Table 1) to amplify the PSCYP3 gene from genomic DNA in a series of overlapping fragments for sequencing. Upon testing a subset of the primer combinations on genomic DNA samples from all four cultivars it was discovered that the PsCYP3 fragments could only be amplified from genomic DNA of the noscapine producing cultivar GSK NOSCAPINE CVS1 but not from genomic DNA of the predominantly morphine (GSK MORPHINE CVS1, GSK MORPHINE) or thebaine (GSK THEBAINE CVS1) producing cultivars (FIG. 7). The PCR amplifications were performed on pools of genomic DNA comprising DNA from four individuals per cultivar using the primer combinations shown in Table 3. This discovery explains why the PSCYP3 is only expressed in the GSK NOSCAPINE CVS1 cultivar and is absent from the transcriptome of the other three cultivars.

Example 16

Segregation Analysis of PSCYP1 and Noscapine Production in an F2 Mapping Population Derived from a Cross between GSK Noscapine CVS1 and GSK Thebaine CVS1.

Cultivar GSK NOSCAPINE CVS1, which produces noscapine, was cross pollinated with cultivar GSK THEBAINE CVS1 which produces negligible amounts of noscapine. Resulting F1 plants were grown to maturity and F2 seed collected. Two hundred and seventy five F2 individuals from the GSK NOSCAPINE CVS1 and GSK THEBAINE CVS1 10 cross were grown to maturity in the field. Leaf material was collected from each individual and used for DNA extraction and analysis. Mature capsules were collected from each individual for alkaloid extraction and analysis.

FIGS. 8*a-c* present the results of the F2 mapping population analysis. The PSCYP1, PSCYP2 and PSCYP3 genes are linked and segregate with noscapine production in the F2 mapping population. The data demonstrate that in the mapping population GSK NOSCAPINE CVS1 levels are present in 61 out of 275 individual F2 plants. The PSCYP1, PSCYP2 and PSCYP3 gene were detected in all of the noscapine containing plants thus confirming that the PSCYP1, PSCYP2 and PSCYP3 genes and noscapine production are linked. Furthermore, all plants in which the PSCYP1, PSCYP2 and PSCYP3 genes were not detected lacked noscapine (The genotyping assay for PSCYP3 failed on 16 samples as indicated by the failure of the internal positive control included in the assay; since these samples were excluded from the segregation analysis of PSCYP3 with the noscapine trait). These data are highly statistically relevant and confirm that the PSCYP1, PSCYP2 and PSCYP3 genes are required for production of GSK NOSCAPINE CVS1 levels of noscapine.

Example 17

Putative Tetrahydrocolumbamine Accumulates in PSCYP2-Silenced Plants

Virus induced gene silencing led to the accumulation of putative tetrahydrocolumbamine in both latex and mature capsules of PSCYP2-silenced plants but not of PSCYP3-silenced plants, PDS-silenced control plants or uninfected plants of GSK NOSCAPINE CVS1 (FIG. 14). The data suggest that PSCYP2 encodes a methylenedioxy-bridge forming enzyme which converts tetrahydrocolumbamine to canadine thus leading to the formation of the methylenedioxybridge present at C-3a'/C-9a' of the isoquinoline moiety of noscapine.

Example 18

Putative Secoberbines Accumulates in PSCYP3-Silenced Plants

Virus induced gene silencing led to the accumulation of putative secoberbine alkaloids in both latex and mature capsules of PSCYP3-silenced plants but not of PSCYP2-silenced plants, PDS-silenced control plants or uninfected plants of GSK NOSCAPINE CVS1 (FIGS. 15 and 16). The mass, assigned molecular formula (C21H23NO6) and fragmentation pattern of the putative secoberbine shown to accumulate in FIG. 15 is consistent with either demethoxy-hydroxymacrantaldehyde or demethoxymacrantoridine. Both of these secoberbines lack a methoxy-group at the carbon of the isoquinoline moiety which is equivalent to the C-4' of noscapine. The mass, assigned molecular formula (C21H25NO6) and fragmentation pattern of the second compound found to accumulate in PSCYP3-silenced plants (FIG. 16) is consistent with two secoberbines, demethoxy-narcotinediol and narcotolinol, respectively. The former compound lacks the methoxy-group at the carbon equivalent to C-4' of noscapine. Together the data suggest that the protein encoded by PSCYP3 hydroxylates the isoquinoline moiety of secoberbines at a position equivalent to C-4' of noscapine thus enabling the formation of the methoxy-group present in noscapine at this position by subsequent 0-methylation. The respective methoxylated derivatives (methoxylated at the carbon equivalent to C-4' of noscapaine) of the putative secoberbines accumulating in PSCYP3-silenced plants have been found in various *Papaver* species producing noscapine (Sariyar and Phillipson (1977) Phytochem. 16: 2009-2013; Sariyar and Shamma (1986) Phytochem. 25: 2403-2406, Sariyar (2002) Pure Appl. Chem. 74: 557-574). They have been implicated, on structural grounds, in the biosynthetic conversion of protoberberines into phthalide-isoquinolines such as noscapine (Sariyar and Shamma (1986) Phytochem. 25: 2403-2406, Sariyar and Phillipson (1977) Phytochem. 16: 2009-2013).

The invention claimed is:

1. An isolated nucleic acid molecule that encodes a cytochrome P450 polypeptide wherein said nucleic acid molecule comprises or consists of a nucleotide sequence selected from the group consisting of:

i) the cDNA nucleotide sequence of SEQ ID NO:1;

ii) a cDNA nucleotide sequence that is degenerate as a result of the genetic code to the cDNA nucleotide sequence defined in (i);

iii) a nucleic acid sequence comprising at least 90% sequence identity with the cDNA nucleotide sequence of SEQ ID NO:1;

iv) a nucleotide sequence that encodes the polypeptide sequence of SEQ ID NO:8; and v) a nucleotide sequence that encodes a polypeptide comprising at least 95% sequence identity to the protein sequence of SEQ ID NO:8.

2. The isolated nucleic acid molecule according to claim 1, wherein said nucleic acid molecule comprises or consists of the nucleotide sequence of SEQ ID NO:1.

3. A vector comprising the nucleic acid molecule encoding the cytochrome P450 polypeptide according to claim 1, wherein said nucleic acid molecule is operably linked to a nucleic acid molecule comprising a promoter sequence.

4. The vector according to claim 3, wherein said nucleic acid sequence comprising a promoter confers constitutive expression on said cytochrome P450 polypeptide.

5. A transgenic cell transformed or transfected with the nucleic acid molecule of claim 1.

6. The transgenic cell according to claim 5, wherein said cell is a plant cell.

7. The transgenic cell according to claim 6, wherein said plant cell is from the family Papaveraceae.

8. The transgenic cell according to claim 7, wherein said plant cell is a *Papaver somniferum* cell.

9. A plant comprising the plant cell of claim 6.

10. The plant according to claim 9, wherein said plant is from the family Papaveraceae.

11. The plant according to claim 10, wherein said plant is *Papaver somniferum.*

12. The transgenic cell according to claim 5, wherein said cell is a microbial cell.

13. The transgenic cell of claim 5, wherein said cell is adapted such that the nucleic acid molecule encoding the cytochrome P450 is over-expressed when compared to a non-transgenic cell or plant of the same species.

14. A nucleic acid molecule comprising a transcription cassette, wherein said cassette comprises the nucleotide sequence of SEQ ID NO:1 or SEQ ID NO:5 and is adapted for expression by provision of at least one promoter operably linked to said nucleotide sequence such that both sense and antisense molecules are transcribed from said cassette.

15. The nucleic acid molecule according to claim 14, wherein said cassette is adapted such that both sense and antisense ribonucleic acid molecules are transcribed from said cassette wherein said sense and antisense nucleic acid molecules are adapted to anneal over at least part or all of their length to form a siRNA or shRNA.

16. The nucleic acid molecule according to claim 15, wherein said cassette is provided with at least two promoters adapted to transcribe both sense and antisense strands of said ribonucleic acid molecule.

17. The nucleic acid molecule according to claim 14, wherein said cassette comprises a nucleic acid molecule wherein said molecule comprises a first part linked to a second part wherein said first and second parts are complementary over at least part of their sequence and further wherein transcription of said nucleic acid molecule produces a ribonucleic acid molecule which forms a double stranded region by complementary base pairing of said first and second parts thereby forming an shRNA.

18. The nucleic acid molecule according to claim 14, wherein said nucleic acid molecule is part of a vector adapted for expression in a plant cell.

19. A plant cell transfected with the nucleic acid molecule claim 14, wherein said cell has reduced expression of said cytochrome P450 polypeptide.

20. A process for the modification of an opiate alkaloid comprising:

i) providing the transgenic plant cell according to claim 19;

ii) cultivating said plant cell to produce a transgenic plant; and optionally iii) harvesting said transgenic plant, or part thereof.

21. The process according to claim 20, wherein said harvested plant part is dried straw and said opiate alkaloid is extracted.

22. A process for the modification of an opiate alkaloid comprising:

i) providing the transgenic microbial cell according to claim 12 that expresses a cytochrome P450 in culture with at least one opiate alkaloid;

ii) cultivating the microbial cell under conditions that modify one or more opiate alkaloids; and optionally iii) isolating said modified alkaloid from the microbial cell or cell culture.

23. The process according to claim 22, wherein said microbial cell is a bacterial cell or fungal/yeast cell.

24. A plant comprising a viral vector that includes the nucleic acid molecule according to claim 1.

25. The plant according to claim 24, wherein said gene is encoded by a nucleic acid molecule comprising a nucleic acid sequence selected from the group consisting of:

i) the nucleic acid molecule comprising or consisting of SEQ ID NO:1 or SEQ ID NO:5;

ii) a nucleic acid molecule comprising a nucleotide sequence that hybridizes under stringent hybridization conditions to a nucleic acid molecule in (i) and which encodes a cytochrome p450 polypeptide; and iii) a nucleic acid molecule that encodes a variant polypeptide that varies from a polypeptide comprising the amino acid sequence as represented in SEQ ID NO:8.

26. A viral vector comprising the nucleic acid molecule of claim 1.

27. A method of gene silencing in a plant, comprising: introducing the viral vector of claim 26 into the plant, thereby inducing gene silencing.

28. The method of claim 27, wherein the plant is from the family Papaveraceae.

29. The isolated nucleic acid molecule of claim 1, wherein the isolated nucleic acid molecule encodes a cytochrome P450 polypeptide having at least 95% sequence identity to the protein sequence in SEQ ID NO:8, wherein said nucleic acid molecule comprises or consists of a nucleotide sequence selected from the group consisting of:

i) the cDNA nucleotide sequence shown in SEQ ID NO:1;

ii) a cDNA nucleotide sequence that is degenerate as a result of the genetic code to the nucleotide sequence defined in (i); and iii) a nucleotide sequence comprising at least 90% sequence identity with the cDNA nucleotide sequence in SEQ ID NO:1.

* * * * *

SEQUENCE LISTING

<160> NUMBER OF SEQ ID NOS: 56

<210> SEQ ID NO 1
<211> LENGTH: 1623
<212> TYPE: DNA
<213> ORGANISM: Papaver somniferum

<400> SEQUENCE: 1
atggagttat tcataaagtt accatttatc caaccaattc ctttcagtat tattcttgtt 60
actacagttt cgattgttct attatacagt gtcttcttct gggttactga taagaaaaag 120
aagaggaaga aagcaccaaa tgctgcaggg gcatggccgt taataggtca tctccgtcta 180
ttgatgaacg acaaggaacc gttgtataga gcactaggga gcatggctga taagtacgga 240
cctgcattca acatccgatt aggtaaccaa gaagttcttg ttgtgagtaa ctgggagatg 300
gtaaaacagt gttttggtaa tcaaaatgat aagctatttt cgaatcgtca aactacatta 360
gctgcaaaat acatgcttaa tcaaacaact tctagcggat tcgcaccata tggaccatat 420
tggagagagc tacgaaagat aatggtgcag caattactct ctaaacaatc tttagaatcg 480
tggaaacatc tgaaaatcaa agagatggat gcttcattta gtaaacttaa cgagttatgc 540
aacaacaacg gtactggaac agctacccta attaggatgg acgaatggtt tgctgagttg 600
acgttcaacg tgatcgcaag aaatgtcttt ggctaccaaa gtggcggaag gtcgacagcg 660
cttacgaacg gagatacgga atcaaagggc gagaggtaca agaaaacatt ggaagaagca 720
cttcatctta tgtcaatttt tgcagtttca gacatatttc caagtctaga gtgggtagat 780
cggttaagag gccttataag gaatatgaaa cgctttggag atgagctaaa ttcaattgca 840

```
gggtgtctta ttgaagagca ccgccaaaag agattacaat ccgtatctaa aagtgataaa    900

ggagttggtg atgaacaaga cttcgttgat gttctcttat cggttgctga aaaatcgcaa    960

cttcctggag atgaccctga tttggtcatc aagtctatga ttctggaaat cgtatcaggt   1020

gggagtgaga ccacatcgtc aaccttaact tgggccctct gtctgttact gaaccatccg   1080

catgtgttaa agaaggcaaa agaggaatta gatacgcacg taggaaaaga taggcatgta   1140

gaagagtcag ataccccctaa gctcgtgtac attaatgcaa ttatcaaaga atcaatgcga   1200

ttgtatccaa acggggcaat gcttgatcgg ttggcgttag aagagtgcga agttggtgga   1260

tttcatgtac cggccggggg acgcttattt gtcaatgttt ggaagattca gagagatccg   1320

agtgtttggg agaatcctct ggagtttaaa ccagagaggt ggtttttgag taatggtgaa   1380

aagatggatg tggattacaa aggtcacaat catgaattca taccatttgg gataggtcgg   1440

aggatgtgcg ctggtatgct ttgggcatcg gaggtgattc atttggtgct gccccgtctt   1500

attcatgggt ttgatatgaa agcagcaagt gccaatggga aagtagatat ggcagaaatg   1560

gcaggcatgg tgatttgttt taagaagaca cctcttgaag ttatggtcaa tcctcgagag   1620

tag                                                                 1623
```

```
<210> SEQ ID NO 2
<211> LENGTH: 1439
<212> TYPE: DNA
<213> ORGANISM: Papaver somniferum

<400> SEQUENCE: 2

atgatcatga gtaacttatg gattcttacg ctcatttcta ccatattagc agtctttgct     60

gctgtgttaa tcattttcag gagaagaata tcagcatcca caacggaatg gcctgttggc    120

ccaaaaatta ccaatcatag gtaacttgca cattcttgga ggcactgctc tccatgtcgt    180

cttacataaa cttgctgaag tttacggcag tgtaatgacg atatggattg gtagttggaa    240

acctgttatt attttccgac tttgatcgag cctgggaagt tcttgttaac aaatcgtcag    300

attattcagc tcgtgaaatg cctgagatca ctaaaatcgg cactgcaaat tggagaacaa    360

tttcaagttc tgattctggc cttttgggcc actcttcgaa aaggtcttca gagtgtagca    420

ttatcgcctc agcatttagc atcgcaaact gcacaccaag agagagatat aataaagttg    480

atcaaaaatt tgaaagacga agcagttcgg aatggttaaa ccacttgatc atctcaagaa    540

agcaactgta agattaatca gtcggttaat ctatggtcag gattttgatg acgataagta    600

tgttgaagat atgcatgacg tgatcgagtt ttgatcgtat tagtggttat gctcaacttg    660

ctgaggtatt ctattatgct aaatatctac caggtcataa gagagctgta actggcgccg    720

aagaagcaaa aagaagagta atagctctgg tgcgtccttt ctcagtcaaa ccctgctact    780

aacacttact tgcattttct caaatcgcaa ctgtatcctg aagaggttat catattcgct    840

atattcgaag cttatctttt aggtgttgat agcacttctt caacactgct gggcactcgc    900

attcttaata cgcgaaccat ctgttcaaga gaaactttat caagagctta agaatttcac    960

agccaataac aatcgcacaa tgctgaaagt cgaagacgtc aacaaattac atatttcaag   1020

ctgttgttaa agaaacaatg aggatgaaac caattgcacc actggcgatt cctcataaag   1080

cttgtaaaga cacttcattg atgggcaaga aagttgataa gggaactaaa gttatgttaa   1140

catcatgctt tacatcatac tgaaaaggtt tggaaagaac cttacaaatt cataccagag   1200

aggtttctgc agaagcacga taaggcgatg gaacaatcac tattaccatt tagtgcaggt   1260
```

-continued agagaatttg gcaggaatgg aattaggaaa acttcagttt agtttttctc ttgctaatct 1320
tgttaatgct tttaaatggt cttgtgtgtc tgatggagtg cttcctgata tgagtgattt 1380
actggggttg ttctgttatg aaaaccccac tcgaagcacg tatagttcct cgtttgtag 1439

<210> SEQ ID NO 3
<211> LENGTH: 1653
<212> TYPE: DNA
<213> ORGANISM: Papaver somniferum

<400> SEQUENCE: 3
atgatgaaca agttattatt tctccaacgg attactgatt ctccttcgac caccattatc 60
agtactttta ttgttacaat aatatccatt gtttttctct acactgtctt gttgataagg 120
acgactaaga ataagcagaa gatagcagca ccaaaagcat cgggggcgtg gccgttcata 180
ggtcatctca aactattcat gaaacaagat actcagtttt acagaactct aggaaccatg 240
tctgataaat acgggtcggt gttcacactt cgattaggaa accaagcaat cctagttgtg 300
agcaactggg agatggtaaa agaatgtttc acaacaaacg acaagtcatt ctcgaatcgt 360
ccaagtacgt taagcactaa atacatgctg aatgacacta attctgtcgt gttttcacct 420
tacggaacgt attggagaga aatgcggaag atattggtgc aaaaactact gatctctaac 480
caaagatcag aggcattgaa aaatctgaaa acgaaagaaa tcgacaactc gtttgtaaag 540
cttaatgatt tatgcaacaa cgatgtcagt ggaggaggca caaaagttag gatggacgaa 600
tggttggctg acatgatgtt caacattatt gctaggatta catttggtta ccaaagcgga 660
ggaggcgatg cacctggcgc ttctacaaca tccaagaatg tcgagagata caagaaaacg 720
ttggacgaga tgtttgttgt tttagcgacg aggtttgcag tttcagatat atttccatct 780
ctggagttta tagaccgatt gagaggtctt gtaaaggata tgaaaatctt gggagacgaa 840
ttaaactcca ttgctggatg ttttattgaa gaacatcgtc aaaagagacg agaatcatta 900
tcctcattgt tatctttgtc aaatgaatcc gttggtgatg aacaagattt cattgatgtt 960
ctcttgtcaa taatggatca gtcacggctt cccggagatg acccagattt tattatcaaa 1020
attatgatcc tggaagcttt tgcaggtggg acggacagtt taagtgcaac cttaacttgg 1080
gtcctctctc tactgctgaa ccacccaaac gtgttaaaga gggcaaggga ggaaatagat 1140
aggcatgtgg aaaacggtaa gcaagtggaa gtgtctgata ttccgaagct cggatacatt 1200
gatgcaataa tcaaagagac gatgagattg tatccagtcg gagcattaag cgaacgatac 1260
acgactgaag aatgcgaggt tggtcggttt aacgtacccg ctggcacacg cttactggtg 1320
aatatatgga agatccacag agacccaagt gtgtgggaga atccatcaga ttttcaacca 1380
gagaggtttt tgtgcagcga taaggtgggt gtggatttat atggccagaa ttatgagctg 1440
ataccatttg ggccggtag gagggtatgt ccggctatag tttcatcact gcagacgatg 1500
cattatgcgt tggcgcgtct tattcaagga tatgaaatga aatcagccag cctcgatggg 1560
aaggtgaata tggaagaaat gatagccatg tcgtgccaca agatgagccc tcttgaagtt 1620
attatcagtc ctcgggagcc gaggcggagt taa 1653

<210> SEQ ID NO 4
<211> LENGTH: 1650
<212> TYPE: DNA
<213> ORGANISM: Papaver somniferum

<400> SEQUENCE: 4
atgaacaagt tattatttct ccaacggatt actgattctc cttcgaccac cattatcagt 60

```
acttttattg ttacaataat atccattgtt tttctctaca ctgtcttgtt gataaggacg    120
actaagaata agcagaagat agcagcacca aaagcatcgg gggcgtggcc gttcataggt    180
catctcaaac tattcatgaa acaagatact cagttttaca gaactctagg aaccatgtct    240
gataaatacg ggtcggtgtt cacacttcga ttaggaaacc aagcaatcct agttgtgagc    300
aactgggaga tggtaaaaga atgtttcaca acaaacgaca agtcattctc gaatcgtcca    360
agtacgttaa gcactaaata catgctgaat gacactaatt ctgtcgtgtt ttcaccttac    420
ggaacgtatt ggagagaaat gcggaagata ttggtgcaaa aactactgat ctctaaccaa    480
agatcagagg cattgaaaaa tctgaaaacg aaagaaatcg acaactcgtt tgtaaagctt    540
aatgatttat gcaacaacga tgtcagtgga ggaggcacaa aagttaggat ggacgaatgg    600
ttggctgaca tgatgttcaa cattattgct aggattacat ttggttacca aagcggagga    660
ggcgatgcac ctggcgcttc tacaacatcc aagaatgtcg agagatacaa gaaaacgttg    720
gacgagatgt ttgttgtttt agcgacgagg tttgcagttt cagatatatt tccatctctg    780
gagtttatag accgattgag aggtcttgta aaggatatga aaatcttggg agacgaatta    840
aactccattg ctggatgttt tattgaagaa catcgtcaaa agagacgaga atcattatcc    900
tcattgttat ctttgtcaaa tgaatccgtt ggtgatgaac aagatttcat tgatgttctc    960
ttgtcaataa tggatcagtc acggcttccc ggagatgacc cagattttat tatcaaaatt   1020
atgatcctgg aagcttttgc aggtgggacg gacagtttaa gtgcaacctt aacttgggtc   1080
ctctctctac tgctgaacca cccaaacgtg ttaaagaggg caagggagga aatagatagg   1140
catgtggaaa acggtaagca agtggaagtg tctgatattc cgaagctcgg atacattgat   1200
gcaataatca aagagacgat gagattgtat ccagtcggag cattaagcga acgatacacg   1260
actgaagaat gcgaggttgg tcggtttaac gtacccgctg gcacacgctt actggtgaat   1320
atatggaaga tccacagaga cccaagtgtg tgggagaatc catcagattt tcaaccagag   1380
aggtttttgt gcagcgataa ggtgggtgtg gatttatatg gccagaatta tgagctgata   1440
ccatttgggg ccggtaggag ggtatgtccg gctatagttt catcactgca gacgatgcat   1500
tatgcgttgg cgcgtcttat tcaaggatat gaaatgaaat cagccagcct cgatgggaag   1560
gtgaatatgg aagaaatgat agccatgtcg tgccacaaga tgagccctct tgaagttatt   1620
atcagtcctc gggagccgag gcggagttaa                                    1650
```

<210> SEQ ID NO 5
<211> LENGTH: 1921
<212> TYPE: DNA
<213> ORGANISM: Papaver somniferum

<400> SEQUENCE: 5

```
cttgagtcat gccttgatat gctcatattt tagtttgtca tattcactat aactataaat     60
ttcaatacaa tttctaaaac tcatcatcat tcaagagaga tacaaatacc ttgatatcct    120
tttatcatca atggagttat tcataaagtt accatttatc caaccaattc ctttcagtat    180
tattcttgtt actacagttt cgattgttct attatacagt gtcttcttct gggttactga    240
taagaaaaag aagaggaaga aagcaccaaa tgctgcaggg gcatggccgt taataggtca    300
tctccgtcta ttgatgaacg acaaggaacc gttgtataga gcactaggga gcatggctga    360
taagtacgga cctgcattca acatccgatt aggtaaccaa gaagttcttg ttgtgagtaa    420
ctgggagatg gtaaaacagt gttttggtaa tcaaaatgat aagctatttt cgaatcgtca    480
```

-continued aactacatta gctgcaaaat acatgcttaa tcaaacaact tctagcggat tcgcaccata 540
tggaccatat tggagagagc tacgaaagat aatggtgcag caattactct ctaaacaatc 600
tttagaatcg tggaaacatc tgaaaatcaa agagatggat gcttcattta gtaaacttaa 660
cgagttatgc aacaacaacg gtactggaac agctacccta attaggatgg acgaatggtt 720
tgctgagttg acgttcaacg tgatcgcaag aaatgtcttt ggctaccaaa gtggcggaag 780
gtcgacagcg cttacgaacg gtaatatgat catactccct caatctgtat caatttaagg 840
aaatcatttt ggtcttgtta ttaacttgaa ttttctatta ggagatacgg aatcaaaggg 900
cgagaggtac aagaaaacat tggaagaagc acttcatctt atgtcaattt ttgcagtttc 960
agacatattt ccaagtctag agtgggtaga tcggttaaga ggccttataa ggaatatgaa 1020
acgctttgga gatgagctaa attcaattgc agggtgtctt attgaagagc accgccaaaa 1080
gagattacaa tccgtatcta aaagtgataa aggagttggt gatgaacaag acttcgttga 1140
tgttctctta tcggttgctg aaaaatcgca acttcctgga gatgaccctg atttggtcat 1200
caagtctatg attctggtta ggctattgat accaagtcta ttgcaatttt ggtttatgtg 1260
cttgttctaa ctttcgttta ctgcatatgg atgtgcagga aatcgtatca ggtgggagtg 1320
agaccacatc gtcaacctta acttgggccc tctgtctgtt actgaaccat ccgcatgtgt 1380
taaagaaggc aaaagaggaa ttagatacgc acgtaggaaa agataggcat gtagaagagt 1440
cagatacccc taagctcgtg tacattaatg caattatcaa agaatcaatg cgattgtatc 1500
caaacggggc aatgcttgat cggttggcgt tagaagagtg cgaagttggt ggatttcatg 1560
taccggccgg gggacgctta tttgtcaatg tttggaagat tcagagagat ccgagtgttt 1620
gggagaatcc tctggagttt aaaccagaga ggtggttttt gagtaatggt gaaaagatgg 1680
atgtggatta caaaggtcac aatcatgaat tcataccatt tgggataggt cggaggatgt 1740
gcgctggtat gctttgggca tcggaggtga ttcatttggt gctgccccgt cttattcatg 1800
ggtttgatat gaaagcagca agtgccaatg ggaaagtaga tatggcagaa atggcaggca 1860
tggtgatttg ttttaagaag acacctcttg aagttatggt caatcctcga gagtagatgt 1920
t 1921

<210> SEQ ID NO 6
<211> LENGTH: 1688
<212> TYPE: DNA
<213> ORGANISM: Papaver somniferum

<400> SEQUENCE: 6
gatgaaattc tttatgcaaa gagtcaatct gactcaagct agctagaata tataccaatc 60
ataaaagaaa tgatcatgag taacttatgg attcttacgc tcatttctac catattagca 120
gtctttgctg ctgtgttaat cattttcagg agaagaatat cagcatccac aacggaatgg 180
cctgttggcc caaaaacatt accaatcata ggtaacttgc acattcttgg aggcactgct 240
ctccatgtcg tcttacataa acttgctgaa gtttacggca gtgtaatgac gatatggatt 300
ggtagttgga aacctgttat tattgtttcc gactttgatc gagcctggga agttcttgtt 360
aacaaatcgt cagattattc agctcgtgaa atgcctgaga tcactaaaat cggcactgca 420
aattggagaa caatttcaag ttctgattct ggtccgtttt gggccactct tcgaaaaggt 480
cttcagagtg tagcattatc gcctcagcat ttagcatcgc aaactgcaca ccaagagaga 540
gatataataa agttgatcaa aaatttgaaa gacgaagcag cttctggaat ggttaaacca 600
cttgatcatc tcaagaaagc aactgtaaga ttaatcagtc ggttaatcta tggtcaggat 660

```
tttgatgacg ataagtatgt tgaagatatg catgacgtga tcgagttttt gattcgtatt    720

agtggttatg ctcaacttgc tgaggtattc tattatgcta aatatctacc aggtcataag    780

agagctgtaa ctggcgccga agaagcaaaa agaagagtaa tagctctggt gcgtcctttt    840

cttcagtcaa accctgctac taacacttac ttgcattttc tcaaatcgca actgtatcct    900

gaagaggtta tcatattcgc tatattcgaa gcttatcttt taggtgttga tagcacttct    960

tcaaccactg catgggcact cgcattctta atacgcgaac catctgttca agagaaactt   1020

tatcaagagc ttaagaattt cacagccaat aacaatcgca caatgctgaa agtcgaagac   1080

gtcaacaaat taccatattt acaagctgtt gttaaagaaa caatgaggat gaaaccaatt   1140

gcaccactgg cgattcctca taaagcttgt aaagacactt cattgatggg caagaaagtt   1200

gataagggaa ctaaagttat ggttaacatt catgctttac atcatactga aaaggtttgg   1260

aaagaacctt acaaattcat accagagagg tttctgcaga agcacgataa ggcgatggaa   1320

caatcactat taccatttag tgcaggtatg agaatttgtg caggaatgga attaggaaaa   1380

cttcagttta gtttttctct tgctaatctt gttaatgctt ttaaatggtc ttgtgtgtct   1440

gatggagtgc ttcctgatat gagtgattta ctggggtttg ttctgttcat gaaaacccca   1500

ctcgaagcac gtatagttcc tcgtttgtag tgatggaaat ttcatctcat gttgttgttt   1560

ctcttcatgt ttactatttc gtactcgttt ggttttggtg taaaaaataa gatctaaact   1620

tccaaatatc attaatgttt acacaaatcg aaatcaatca actatgttat gaaaattagt   1680

gttttcgc                                                             1688
```

<210> SEQ ID NO 7
<211> LENGTH: 2918
<212> TYPE: DNA
<213> ORGANISM: Papaver somniferum

<400> SEQUENCE: 7

```
aagtgtgcca ctaatctact gctagtgcta ctgctcactg acacttacac atatgattga     60

tttatggcta aacaggatga ccactaaatt tattttggaa agcggagtga attaattaag    120

tggcacattt tccatgagaa ttattgatgg catgcattta gatgaacaag atacaccaaa    180

tgtagtgact gaacaagatg ctcgatccta accccacctg caactttagc taaactttaa    240

taattacatg tcttatcttt ttattgaatc attttatcta tcaatggatg ctgatcaata    300

atatcatata tctttgcttt ttcttcaatc atttagatga acaaaaaaca caataagtgt    360

agtggttgtt cataacccca ccttcaactc attcttccct ttaataacaa atatctttgc    420

tttttctcca atcatttact tgaacaacca acactagtaa gtgtagtggt ttctcataac    480

cccacctgca atttttgctt acctttaata acatatatct ttgattttct tcgatcattt    540

tagctaccaa tggatgctga tccaaaaagt tatggcaaaa agagacaacg tgatcgaaca    600

cgagcctctc gtgcaccaca gcatcaaggt ttgtggaaat taaccgcttg taaaaaatgg    660

agtgcgtgat cataatgagg tattgctaag atatagtatc aactttagtg aactgggcca    720

acaaaactca cgagttgttg aaaattggag attatattta taagataaaa gggtcactcc    780

ctacacaacg acttgcactg caagtgaaaa agaaaaaaaa caaacaacct caatctagct    840

agagtcgtga aaaagttttg tgcgactgtt atttagttaa ttataaaatt tcaatgaagt    900

cgttaatgat gaacaagtta ttatttctcc aacggattac tgattctcct tcgaccacca    960

ttatcagtac ttttattgtt acaataatat ccattgtttt tctctacact gtcttgttga   1020
```

-continued

```
taaggacgac taagaataag cagaagatag cagcaccaaa agcatcgggg gcgtggccgt   1080

tcataggtca tctcaaacta ttcatgaaac aagatactca gttttacaga actctaggaa   1140

ccatgtctga taaatacggg tcggtgttca cacttcgatt aggaaaccaa gcaatcctag   1200

ttgtgagcaa ctgggagatg gtaaaagaat gtttcacaac aaacgacaag tcattctcga   1260

atcgtccaag tacgttaagc actaaataca tgctgaatga cactaattct gtcgtgtttt   1320

caccttacgg aacgtattgg agagaaatgc ggaagatatt ggtgcaaaaa ctactgatct   1380

ctaaccaaag atcagaggca ttgaaaaatc tgaaaacgaa agaaatcgac aactcgtttg   1440

taaagcttaa tgatttatgc aacaacgatg tcagtggagg aggcacaaaa gttaggatgg   1500

acgaatggtt ggctgacatg atgttcaaca ttattgctag gattacattt ggttaccaaa   1560

gcggaggagg cgatgcacct ggtatgtgat catcaaattt tcgttaaaac caaattaact   1620

tgtactatat cttatgttta catgttatat tgatcacttt gacacgttct gatcattttc   1680

acaaatcgaa ttaggcgctt ctacaacatc caagaatgtc gagagataca agaaaacgtt   1740

ggacgagatg tttgttgttt tagcgacgag gtttgcagtt tcagatatat ttccatctct   1800

ggagtttata gaccgattga gaggtcttgt aaaggatatg aaaatcttgg gagacgaatt   1860

aaactccatt gctggatgtt ttattgaaga acatcgtcaa aagagacgag aatcattatc   1920

ctcattgtta tctttgtcaa atgaatccgt tggtgatgaa caagatttca ttgatgttct   1980

cttgtcaata atggatcagt cacggcttcc cggagatgac ccagatttta ttatcaaaat   2040

tatgatcctg gtaacatata ttacaacagt atttctttaa gttatggatt aatggatgtc   2100

gtaaccatga atatttttct gatctggata aatgtaatcc ggaactaata tatgaatatt   2160

gttgacgcag gaagcttttg caggtgggac ggacagttta agtgcaacct taacttgggt   2220

cctctctcta ctgctgaacc acccaaacgt gttaaagagg gcaagggagg aaatagatag   2280

gcatgtggaa aacggtaagc aagtggaagt gtctgatatt ccgaagctcg gatacattga   2340

tgcaataatc aaagagacga tgagattgta tccagtcgga gcattaagcg aacgatacac   2400

gactgaagaa tgcgaggttg gtcggtttaa cgtacccgct ggcacacgct tactggtgaa   2460

tatatggaag atccacagag acccaagtgt gtgggagaat ccatcagatt ttcaaccaga   2520

gaggtttttg tgcagcgata aggtgggtgt ggatttatat ggccagaatt atgagctgat   2580

accatttggg gccggtagga gggtatgtcc ggctatagtt tcatcactgc agacgatgca   2640

ttatgcgttg gcgcgtctta ttcaaggata tgaaatgaaa tcagccagcc tcgatgggaa   2700

ggtgaatatg gaagaaatga tagccatgtc gtgccacaag atgagccctc ttgaagttat   2760

tatcagtcct cgggagccga ggcggagtta aatcttatgt tccaatttta cattagcatc   2820

tttgattatg aaatgtattg ctcttaagtt tctttttgt tttttatatt tttaagcttg   2880

tatgtgatca tcagcgaaaa tgatgatgac agaatcgt                          2918
```

<210> SEQ ID NO 8
<211> LENGTH: 540
<212> TYPE: PRT
<213> ORGANISM: Papaver somniferum

<400> SEQUENCE: 8

```
Met Glu Leu Phe Ile Lys Leu Pro Phe Ile Gln Pro Ile Pro Phe Ser
1               5                   10                  15

Ile Ile Leu Val Thr Thr Val Ser Ile Val Leu Leu Tyr Ser Val Phe
            20                  25                  30

Phe Trp Val Thr Asp Lys Lys Lys Lys Arg Lys Lys Ala Pro Asn Ala
```

-continued

```
        35                  40                  45

Ala Gly Ala Trp Pro Leu Ile Gly His Leu Arg Leu Leu Met Asn Asp
    50                  55                  60

Lys Glu Pro Leu Tyr Arg Ala Leu Gly Ser Met Ala Asp Lys Tyr Gly
65                  70                  75                  80

Pro Ala Phe Asn Ile Arg Leu Gly Asn Gln Glu Val Leu Val Val Ser
                85                  90                  95

Asn Trp Glu Met Val Lys Gln Cys Phe Gly Asn Gln Asn Asp Lys Leu
            100                 105                 110

Phe Ser Asn Arg Gln Thr Thr Leu Ala Ala Lys Tyr Met Leu Asn Gln
        115                 120                 125

Thr Thr Ser Ser Gly Phe Ala Pro Tyr Gly Pro Tyr Trp Arg Glu Leu
    130                 135                 140

Arg Lys Ile Met Val Gln Gln Leu Leu Ser Lys Gln Ser Leu Glu Ser
145                 150                 155                 160

Trp Lys His Leu Lys Ile Lys Glu Met Asp Ala Ser Phe Ser Lys Leu
                165                 170                 175

Asn Glu Leu Cys Asn Asn Asn Gly Thr Gly Thr Ala Thr Leu Ile Arg
            180                 185                 190

Met Asp Glu Trp Phe Ala Glu Leu Thr Phe Asn Val Ile Ala Arg Asn
        195                 200                 205

Val Phe Gly Tyr Gln Ser Gly Gly Arg Ser Thr Ala Leu Thr Asn Gly
    210                 215                 220

Asp Thr Glu Ser Lys Gly Glu Arg Tyr Lys Lys Thr Leu Glu Glu Ala
225                 230                 235                 240

Leu His Leu Met Ser Ile Phe Ala Val Ser Asp Ile Phe Pro Ser Leu
                245                 250                 255

Glu Trp Val Asp Arg Leu Arg Gly Leu Ile Arg Asn Met Lys Arg Phe
            260                 265                 270

Gly Asp Glu Leu Asn Ser Ile Ala Gly Cys Leu Ile Glu Glu His Arg
        275                 280                 285

Gln Lys Arg Leu Gln Ser Val Ser Lys Ser Asp Lys Gly Val Gly Asp
    290                 295                 300

Glu Gln Asp Phe Val Asp Val Leu Leu Ser Val Ala Glu Lys Ser Gln
305                 310                 315                 320

Leu Pro Gly Asp Asp Pro Asp Leu Val Ile Lys Ser Met Ile Leu Glu
                325                 330                 335

Ile Val Ser Gly Gly Ser Glu Thr Thr Ser Ser Thr Leu Thr Trp Ala
            340                 345                 350

Leu Cys Leu Leu Leu Asn His Pro His Val Leu Lys Lys Ala Lys Glu
        355                 360                 365

Glu Leu Asp Thr His Val Gly Lys Asp Arg His Val Glu Glu Ser Asp
    370                 375                 380

Thr Pro Lys Leu Val Tyr Ile Asn Ala Ile Ile Lys Glu Ser Met Arg
385                 390                 395                 400

Leu Tyr Pro Asn Gly Ala Met Leu Asp Arg Leu Ala Leu Glu Glu Cys
                405                 410                 415

Glu Val Gly Gly Phe His Val Pro Ala Gly Gly Arg Leu Phe Val Asn
            420                 425                 430

Val Trp Lys Ile Gln Arg Asp Pro Ser Val Trp Glu Asn Pro Leu Glu
        435                 440                 445

Phe Lys Pro Glu Arg Trp Phe Leu Ser Asn Gly Glu Lys Met Asp Val
    450                 455                 460
```

```
Asp Tyr Lys Gly His Asn His Glu Phe Ile Pro Phe Gly Ile Gly Arg
465                 470                 475                 480

Arg Met Cys Ala Gly Met Leu Trp Ala Ser Glu Val Ile His Leu Val
                485                 490                 495

Leu Pro Arg Leu Ile His Gly Phe Asp Met Lys Ala Ala Ser Ala Asn
            500                 505                 510

Gly Lys Val Asp Met Ala Glu Met Ala Gly Met Val Ile Cys Phe Lys
        515                 520                 525

Lys Thr Pro Leu Glu Val Met Val Asn Pro Arg Glu
    530                 535                 540


<210> SEQ ID NO 9
<211> LENGTH: 486
<212> TYPE: PRT
<213> ORGANISM: Papaver somniferum

<400> SEQUENCE: 9

Met Ile Met Ser Asn Leu Trp Ile Leu Thr Leu Ile Ser Thr Ile Leu
1               5                   10                  15

Ala Val Phe Ala Ala Val Leu Ile Ile Phe Arg Arg Arg Ile Ser Ala
            20                  25                  30

Ser Thr Thr Glu Trp Pro Val Gly Pro Lys Thr Leu Pro Ile Ile Gly
        35                  40                  45

Asn Leu His Ile Leu Gly Gly Thr Ala Leu His Val Val Leu His Lys
    50                  55                  60

Leu Ala Glu Val Tyr Gly Ser Val Met Thr Ile Trp Ile Gly Ser Trp
65                  70                  75                  80

Lys Pro Val Ile Ile Val Ser Asp Phe Asp Arg Ala Trp Glu Val Leu
                85                  90                  95

Val Asn Lys Ser Ser Asp Tyr Ser Ala Arg Glu Met Pro Glu Ile Thr
            100                 105                 110

Lys Ile Gly Thr Ala Asn Trp Arg Thr Ile Ser Ser Ser Asp Ser Gly
        115                 120                 125

Pro Phe Trp Ala Thr Leu Arg Lys Gly Leu Gln Ser Val Ala Leu Ser
    130                 135                 140

Pro Gln His Leu Ala Ser Gln Thr Ala His Gln Glu Arg Asp Ile Ile
145                 150                 155                 160

Lys Leu Ile Lys Asn Leu Lys Asp Glu Ala Ala Ser Gly Met Val Lys
                165                 170                 175

Pro Leu Asp His Leu Lys Lys Ala Thr Val Arg Leu Ile Ser Arg Leu
            180                 185                 190

Ile Tyr Gly Gln Asp Phe Asp Asp Asp Lys Tyr Val Glu Asp Met His
        195                 200                 205

Asp Val Ile Glu Phe Leu Ile Arg Ile Ser Gly Tyr Ala Gln Leu Ala
    210                 215                 220

Glu Val Phe Tyr Tyr Ala Lys Tyr Leu Pro Gly His Lys Arg Ala Val
225                 230                 235                 240

Thr Gly Ala Glu Glu Ala Lys Arg Arg Val Ile Ala Leu Val Arg Pro
                245                 250                 255

Phe Leu Gln Ser Asn Pro Ala Thr Asn Thr Tyr Leu His Phe Leu Lys
            260                 265                 270

Ser Gln Leu Tyr Pro Glu Glu Val Ile Ile Phe Ala Ile Phe Glu Ala
        275                 280                 285

Tyr Leu Leu Gly Val Asp Ser Thr Ser Ser Thr Thr Ala Trp Ala Leu
```

```
    290                 295                 300

Ala Phe Leu Ile Arg Glu Pro Ser Val Gln Glu Lys Leu Tyr Gln Glu
305                 310                 315                 320

Leu Lys Asn Phe Thr Ala Asn Asn Asn Arg Thr Met Leu Lys Val Glu
                325                 330                 335

Asp Val Asn Lys Leu Pro Tyr Leu Gln Ala Val Val Lys Glu Thr Met
            340                 345                 350

Arg Met Lys Pro Ile Ala Pro Leu Ala Ile Pro His Lys Ala Cys Lys
        355                 360                 365

Asp Thr Ser Leu Met Gly Lys Lys Val Asp Lys Gly Thr Lys Val Met
    370                 375                 380

Val Asn Ile His Ala Leu His His Thr Glu Lys Val Trp Lys Glu Pro
385                 390                 395                 400

Tyr Lys Phe Ile Pro Glu Arg Phe Leu Gln Lys His Asp Lys Ala Met
                405                 410                 415

Glu Gln Ser Leu Leu Pro Phe Ser Ala Gly Met Arg Ile Cys Ala Gly
            420                 425                 430

Met Glu Leu Gly Lys Leu Gln Phe Ser Phe Ser Leu Ala Asn Leu Val
        435                 440                 445

Asn Ala Phe Lys Trp Ser Cys Val Ser Asp Gly Val Leu Pro Asp Met
    450                 455                 460

Ser Asp Leu Leu Gly Phe Val Leu Phe Met Lys Thr Pro Leu Glu Ala
465                 470                 475                 480

Arg Ile Val Pro Arg Leu
                485


<210> SEQ ID NO 10
<211> LENGTH: 550
<212> TYPE: PRT
<213> ORGANISM: Papaver somniferum

<400> SEQUENCE: 10

Met Met Asn Lys Leu Leu Phe Leu Gln Arg Ile Thr Asp Ser Pro Ser
1               5                   10                  15

Thr Thr Ile Ile Ser Thr Phe Ile Val Thr Ile Ile Ser Ile Val Phe
            20                  25                  30

Leu Tyr Thr Val Leu Leu Ile Arg Thr Thr Lys Asn Lys Gln Lys Ile
        35                  40                  45

Ala Ala Pro Lys Ala Ser Gly Ala Trp Pro Phe Ile Gly His Leu Lys
    50                  55                  60

Leu Phe Met Lys Gln Asp Thr Gln Phe Tyr Arg Thr Leu Gly Thr Met
65                  70                  75                  80

Ser Asp Lys Tyr Gly Ser Val Phe Thr Leu Arg Leu Gly Asn Gln Ala
                85                  90                  95

Ile Leu Val Val Ser Asn Trp Glu Met Val Lys Glu Cys Phe Thr Thr
            100                 105                 110

Asn Asp Lys Ser Phe Ser Asn Arg Pro Ser Thr Leu Ser Thr Lys Tyr
        115                 120                 125

Met Leu Asn Asp Thr Asn Ser Val Val Phe Ser Pro Tyr Gly Thr Tyr
    130                 135                 140

Trp Arg Glu Met Arg Lys Ile Leu Val Gln Lys Leu Leu Ile Ser Asn
145                 150                 155                 160

Gln Arg Ser Glu Ala Leu Lys Asn Leu Lys Thr Lys Glu Ile Asp Asn
                165                 170                 175
```

```
Ser Phe Val Lys Leu Asn Asp Leu Cys Asn Asn Asp Val Ser Gly Gly
            180                 185                 190

Gly Thr Lys Val Arg Met Asp Glu Trp Leu Ala Asp Met Met Phe Asn
        195                 200                 205

Ile Ile Ala Arg Ile Thr Phe Gly Tyr Gln Ser Gly Gly Gly Asp Ala
    210                 215                 220

Pro Gly Ala Ser Thr Thr Ser Lys Asn Val Glu Arg Tyr Lys Lys Thr
225                 230                 235                 240

Leu Asp Glu Met Phe Val Val Leu Ala Thr Arg Phe Ala Val Ser Asp
                245                 250                 255

Ile Phe Pro Ser Leu Glu Phe Ile Asp Arg Leu Arg Gly Leu Val Lys
            260                 265                 270

Asp Met Lys Ile Leu Gly Asp Glu Leu Asn Ser Ile Ala Gly Cys Phe
        275                 280                 285

Ile Glu Glu His Arg Gln Lys Arg Arg Glu Ser Leu Ser Ser Leu Leu
    290                 295                 300

Ser Leu Ser Asn Glu Ser Val Gly Asp Glu Gln Asp Phe Ile Asp Val
305                 310                 315                 320

Leu Leu Ser Ile Met Asp Gln Ser Arg Leu Pro Gly Asp Asp Pro Asp
                325                 330                 335

Phe Ile Ile Lys Ile Met Ile Leu Glu Ala Phe Ala Gly Gly Thr Asp
            340                 345                 350

Ser Leu Ser Ala Thr Leu Thr Trp Val Leu Ser Leu Leu Leu Asn His
        355                 360                 365

Pro Asn Val Leu Lys Arg Ala Arg Glu Glu Ile Asp Arg His Val Glu
    370                 375                 380

Asn Gly Lys Gln Val Glu Val Ser Asp Ile Pro Lys Leu Gly Tyr Ile
385                 390                 395                 400

Asp Ala Ile Ile Lys Glu Thr Met Arg Leu Tyr Pro Val Gly Ala Leu
                405                 410                 415

Ser Glu Arg Tyr Thr Thr Glu Glu Cys Glu Val Gly Arg Phe Asn Val
            420                 425                 430

Pro Ala Gly Thr Arg Leu Leu Val Asn Ile Trp Lys Ile His Arg Asp
        435                 440                 445

Pro Ser Val Trp Glu Asn Pro Ser Asp Phe Gln Pro Glu Arg Phe Leu
    450                 455                 460

Cys Ser Asp Lys Val Gly Val Asp Leu Tyr Gly Gln Asn Tyr Glu Leu
465                 470                 475                 480

Ile Pro Phe Gly Ala Gly Arg Arg Val Cys Pro Ala Ile Val Ser Ser
                485                 490                 495

Leu Gln Thr Met His Tyr Ala Leu Ala Arg Leu Ile Gln Gly Tyr Glu
            500                 505                 510

Met Lys Ser Ala Ser Leu Asp Gly Lys Val Asn Met Glu Glu Met Ile
        515                 520                 525

Ala Met Ser Cys His Lys Met Ser Pro Leu Glu Val Ile Ile Ser Pro
    530                 535                 540

Arg Glu Pro Arg Arg Ser
545                 550
```

<210> SEQ ID NO 11
<211> LENGTH: 549
<212> TYPE: PRT
<213> ORGANISM: Papaver somniferum

<400> SEQUENCE: 11

-continued

```
Met Asn Lys Leu Leu Phe Leu Gln Arg Ile Thr Asp Ser Pro Ser Thr
1               5                   10                  15

Thr Ile Ile Ser Thr Phe Ile Val Thr Ile Ile Ser Ile Val Phe Leu
            20                  25                  30

Tyr Thr Val Leu Leu Ile Arg Thr Thr Lys Asn Lys Gln Lys Ile Ala
        35                  40                  45

Ala Pro Lys Ala Ser Gly Ala Trp Pro Phe Ile Gly His Leu Lys Leu
    50                  55                  60

Phe Met Lys Gln Asp Thr Gln Phe Tyr Arg Thr Leu Gly Thr Met Ser
65                  70                  75                  80

Asp Lys Tyr Gly Ser Val Phe Thr Leu Arg Leu Gly Asn Gln Ala Ile
                85                  90                  95

Leu Val Val Ser Asn Trp Glu Met Val Lys Glu Cys Phe Thr Thr Asn
            100                 105                 110

Asp Lys Ser Phe Ser Asn Arg Pro Ser Thr Leu Ser Thr Lys Tyr Met
        115                 120                 125

Leu Asn Asp Thr Asn Ser Val Val Phe Ser Pro Tyr Gly Thr Tyr Trp
    130                 135                 140

Arg Glu Met Arg Lys Ile Leu Val Gln Lys Leu Leu Ile Ser Asn Gln
145                 150                 155                 160

Arg Ser Glu Ala Leu Lys Asn Leu Lys Thr Lys Glu Ile Asp Asn Ser
                165                 170                 175

Phe Val Lys Leu Asn Asp Leu Cys Asn Asn Asp Val Ser Gly Gly Gly
            180                 185                 190

Thr Lys Val Arg Met Asp Glu Trp Leu Ala Asp Met Met Phe Asn Ile
        195                 200                 205

Ile Ala Arg Ile Thr Phe Gly Tyr Gln Ser Gly Gly Gly Asp Ala Pro
    210                 215                 220

Gly Ala Ser Thr Thr Ser Lys Asn Val Glu Arg Tyr Lys Lys Thr Leu
225                 230                 235                 240

Asp Glu Met Phe Val Val Leu Ala Thr Arg Phe Ala Val Ser Asp Ile
                245                 250                 255

Phe Pro Ser Leu Glu Phe Ile Asp Arg Leu Arg Gly Leu Val Lys Asp
            260                 265                 270

Met Lys Ile Leu Gly Asp Glu Leu Asn Ser Ile Ala Gly Cys Phe Ile
        275                 280                 285

Glu Glu His Arg Gln Lys Arg Arg Glu Ser Leu Ser Ser Leu Leu Ser
    290                 295                 300

Leu Ser Asn Glu Ser Val Gly Asp Glu Gln Asp Phe Ile Asp Val Leu
305                 310                 315                 320

Leu Ser Ile Met Asp Gln Ser Arg Leu Pro Gly Asp Asp Pro Asp Phe
                325                 330                 335

Ile Ile Lys Ile Met Ile Leu Glu Ala Phe Ala Gly Gly Thr Asp Ser
            340                 345                 350

Leu Ser Ala Thr Leu Thr Trp Val Leu Ser Leu Leu Leu Asn His Pro
        355                 360                 365

Asn Val Leu Lys Arg Ala Arg Glu Glu Ile Asp Arg His Val Glu Asn
    370                 375                 380

Gly Lys Gln Val Glu Val Ser Asp Ile Pro Lys Leu Gly Tyr Ile Asp
385                 390                 395                 400

Ala Ile Ile Lys Glu Thr Met Arg Leu Tyr Pro Val Gly Ala Leu Ser
                405                 410                 415
```

-continued

```
Glu Arg Tyr Thr Thr Glu Glu Cys Glu Val Gly Arg Phe Asn Val Pro
            420                 425                 430

Ala Gly Thr Arg Leu Leu Val Asn Ile Trp Lys Ile His Arg Asp Pro
        435                 440                 445

Ser Val Trp Glu Asn Pro Ser Asp Phe Gln Pro Glu Arg Phe Leu Cys
    450                 455                 460

Ser Asp Lys Val Gly Val Asp Leu Tyr Gly Gln Asn Tyr Glu Leu Ile
465                 470                 475                 480

Pro Phe Gly Ala Gly Arg Arg Val Cys Pro Ala Ile Val Ser Ser Leu
                485                 490                 495

Gln Thr Met His Tyr Ala Leu Ala Arg Leu Ile Gln Gly Tyr Glu Met
            500                 505                 510

Lys Ser Ala Ser Leu Asp Gly Lys Val Asn Met Glu Glu Met Ile Ala
        515                 520                 525

Met Ser Cys His Lys Met Ser Pro Leu Glu Val Ile Ile Ser Pro Arg
    530                 535                 540

Glu Pro Arg Arg Ser
545
```

<210> SEQ ID NO 12
<211> LENGTH: 622
<212> TYPE: DNA
<213> ORGANISM: Papaver somniferum

<400> SEQUENCE: 12

```
gaggtgttca ttgccatgtc aaaggcatta aacttcataa acccagatga gctttcgatg      60

cagtgcattt tgatagcttt gaaccgtttc cttcaggaaa agcatggttc caagatggcc     120

tttttagatg gtaatcctcc cgagagactt tgcaagccgg tcgtggatca tatagagtca     180

cttggcggtg aagtccgtct caattccagg attaaaaaga ttgagcttaa aaaagatggt     240

actgtgaaac gtctaatgct caccaacggt gatgcaatag aaggagatgc ttatgtcatt     300

gcaaccccag tggacatcct aaagctgctt atacccgagg agtggaaaga agttgggtac     360

tttaaaagat tggataaatt agttggagtt cctgtgatta acgtccatat atggtttgac     420

aggaaattga aaaatacata tgatcatctt ctcttcagca gaagtcccct cttaagcgta     480

tacgctgaca tgtcagtgac atgcaaggaa tattatgacc caaacaaatc catgcttgag     540

ttggtatttg cacccgctga ggaatggatc tcgcgcagtg actctgaaat tattgaagct     600

actatgcagg agcttgcgaa ac                                              622
```

<210> SEQ ID NO 13
<211> LENGTH: 119
<212> TYPE: DNA
<213> ORGANISM: Papaver somniferum

<400> SEQUENCE: 13

```
atgatcatga gtaacttatg gattcttacg ctcatttcta ccatattagc agtctttgct      60

gctgtgttaa tcattttcag gagaagaata tcagcatcca caacggaatg gcctgttgg      119
```

<210> SEQ ID NO 14
<211> LENGTH: 196
<212> TYPE: DNA
<213> ORGANISM: Papaver somniferum

<400> SEQUENCE: 14

```
taggagggta tgtccggcta tagtttcatc actgcagacg atgcattatg cgttggcgcg      60
```

-continued

```
tcttattcaa ggatatgaaa tgaaatcagc cagcctcgat gggaaggtga atatggaaga    120

aatgatagcc atgtcgtgcc acaagatgag ccctcttgaa gttattatca gtcctcggga    180

gccgaggcgg agttaa                                                    196


<210> SEQ ID NO 15
<211> LENGTH: 22
<212> TYPE: DNA
<213> ORGANISM: Papaver somniferum

<400> SEQUENCE: 15

cttgagtcat gccttgatat gc                                              22


<210> SEQ ID NO 16
<211> LENGTH: 21
<212> TYPE: DNA
<213> ORGANISM: Papaver somniferum

<400> SEQUENCE: 16

ttgatgaacg acaaggaacc g                                               21


<210> SEQ ID NO 17
<211> LENGTH: 23
<212> TYPE: DNA
<213> ORGANISM: Papaver somniferum

<400> SEQUENCE: 17

gctacgaaag ataatggtgc agc                                             23


<210> SEQ ID NO 18
<211> LENGTH: 19
<212> TYPE: DNA
<213> ORGANISM: Papaver somniferum

<400> SEQUENCE: 18

tcgacagcgc ttacgaacg                                                  19


<210> SEQ ID NO 19
<211> LENGTH: 25
<212> TYPE: DNA
<213> ORGANISM: Papaver somniferum

<400> SEQUENCE: 19

gaaccattaa acacttgagt catgc                                           25


<210> SEQ ID NO 20
<211> LENGTH: 39
<212> TYPE: DNA
<213> ORGANISM: Papaver somniferum

<400> SEQUENCE: 20

gcatttggtg ctttcttcct cttctttttc ttatcagta                            39


<210> SEQ ID NO 21
<211> LENGTH: 20
<212> TYPE: DNA
<213> ORGANISM: Papaver somniferum

<400> SEQUENCE: 21

agcaaaccat tcgtccatcc                                                 20


<210> SEQ ID NO 22
<211> LENGTH: 22
```

<212> TYPE: DNA
<213> ORGANISM: Papaver somniferum

<400> SEQUENCE: 22
tgcaattgaa tttagctcat ct 22

<210> SEQ ID NO 23
<211> LENGTH: 26
<212> TYPE: DNA
<213> ORGANISM: Papaver somniferum

<400> SEQUENCE: 23
attcatgatt gtgacctttg taatcc 26

<210> SEQ ID NO 24
<211> LENGTH: 21
<212> TYPE: DNA
<213> ORGANISM: Papaver somniferum

<400> SEQUENCE: 24
tacgacaggt tgctagcttg g 21

<210> SEQ ID NO 25
<211> LENGTH: 27
<212> TYPE: DNA
<213> ORGANISM: Papaver somniferum

<400> SEQUENCE: 25
caaagagtca atctgactca agctagc 27

<210> SEQ ID NO 26
<211> LENGTH: 26
<212> TYPE: DNA
<213> ORGANISM: Papaver somniferum

<400> SEQUENCE: 26
tgaaatgcct gagatcacta aaatcg 26

<210> SEQ ID NO 27
<211> LENGTH: 28
<212> TYPE: DNA
<213> ORGANISM: Papaver somniferum

<400> SEQUENCE: 27
tcaaaccctg ctactaacac ttacttgc 28

<210> SEQ ID NO 28
<211> LENGTH: 24
<212> TYPE: DNA
<213> ORGANISM: Papaver somniferum

<400> SEQUENCE: 28
tgtaaagaca cttcattgat gggc 24

<210> SEQ ID NO 29
<211> LENGTH: 27
<212> TYPE: DNA
<213> ORGANISM: Papaver somniferum

<400> SEQUENCE: 29
gagatgatca agtggtttaa ccattcc 27

<210> SEQ ID NO 30

<211> LENGTH: 18
<212> TYPE: DNA
<213> ORGANISM: Papaver somniferum

<400> SEQUENCE: 30
cgagtgccca tgcagtgg 18

<210> SEQ ID NO 31
<211> LENGTH: 23
<212> TYPE: DNA
<213> ORGANISM: Papaver somniferum

<400> SEQUENCE: 31
cactccatca gacacacaag acc 23

<210> SEQ ID NO 32
<211> LENGTH: 32
<212> TYPE: DNA
<213> ORGANISM: Papaver somniferum

<400> SEQUENCE: 32
gtaaacatta atgatatttg gaagtttaga tc 32

<210> SEQ ID NO 33
<211> LENGTH: 31
<212> TYPE: DNA
<213> ORGANISM: Papaver somniferum

<400> SEQUENCE: 33
ttcgatttgt gtaaacatta atgatatttg g 31

<210> SEQ ID NO 34
<211> LENGTH: 27
<212> TYPE: DNA
<213> ORGANISM: Papaver somniferum

<400> SEQUENCE: 34
gttatctttg tcaaatgaat ccgttgg 27

<210> SEQ ID NO 35
<211> LENGTH: 24
<212> TYPE: DNA
<213> ORGANISM: Papaver somniferum

<400> SEQUENCE: 35
aataatggat cagtcacggc ttcc 24

<210> SEQ ID NO 36
<211> LENGTH: 24
<212> TYPE: DNA
<213> ORGANISM: Papaver somniferum

<400> SEQUENCE: 36
atgtggaaaa cggtaagcaa gtgg 24

<210> SEQ ID NO 37
<211> LENGTH: 27
<212> TYPE: DNA
<213> ORGANISM: Papaver somniferum

<400> SEQUENCE: 37
aatccatcag attttcaacc agagagg 27

-continued

<210> SEQ ID NO 38
<211> LENGTH: 25
<212> TYPE: DNA
<213> ORGANISM: Papaver somniferum

<400> SEQUENCE: 38
acgattctgt catcatcatt ttcgc 25

<210> SEQ ID NO 39
<211> LENGTH: 24
<212> TYPE: DNA
<213> ORGANISM: Papaver somniferum

<400> SEQUENCE: 39
agtcgtgtat cgttcgctta atgc 24

<210> SEQ ID NO 40
<211> LENGTH: 28
<212> TYPE: DNA
<213> ORGANISM: Papaver somniferum

<400> SEQUENCE: 40
ggcttcccgg agatgaccca gattttat 28

<210> SEQ ID NO 41
<211> LENGTH: 38
<212> TYPE: DNA
<213> ORGANISM: Papaver somniferum

<400> SEQUENCE: 41
ttgttatttt catgactatt accaccagct tcctctta 38

<210> SEQ ID NO 42
<211> LENGTH: 30
<212> TYPE: DNA
<213> ORGANISM: Papaver somniferum

<400> SEQUENCE: 42
agtggaggag gcacaaaagt taggatggac 30

<210> SEQ ID NO 43
<211> LENGTH: 29
<212> TYPE: DNA
<213> ORGANISM: Papaver somniferum

<400> SEQUENCE: 43
ccatgtctga taaatacggg tcggtgttc 29

<210> SEQ ID NO 44
<211> LENGTH: 36
<212> TYPE: DNA
<213> ORGANISM: Papaver somniferum

<400> SEQUENCE: 44
ttgttgataa ggacgactaa gaataagcag aagata 36

<210> SEQ ID NO 45
<211> LENGTH: 29
<212> TYPE: DNA
<213> ORGANISM: Papaver somniferum

<400> SEQUENCE: 45
catgcctatc tatttcctcc cttgccctc 29

<210> SEQ ID NO 46
<211> LENGTH: 28
<212> TYPE: DNA
<213> ORGANISM: Papaver somniferum

<400> SEQUENCE: 46
tgtcagccaa ccattcgtcc atcctaac 28

<210> SEQ ID NO 47
<211> LENGTH: 31
<212> TYPE: DNA
<213> ORGANISM: Papaver somniferum

<400> SEQUENCE: 47
tgttcgatca cgttgtctct ttttgccata a 31

<210> SEQ ID NO 48
<211> LENGTH: 38
<212> TYPE: DNA
<213> ORGANISM: Papaver somniferum

<400> SEQUENCE: 48
taacaataaa agtactgata atggtggtcg aaggagaa 38

<210> SEQ ID NO 49
<211> LENGTH: 30
<212> TYPE: DNA
<213> ORGANISM: Papaver somniferum

<400> SEQUENCE: 49
ataatggtgg tcgaaggaga atcagtaatc 30

<210> SEQ ID NO 50
<211> LENGTH: 22
<212> TYPE: DNA
<213> ORGANISM: Papaver somniferum

<400> SEQUENCE: 50
gaggtgttca ttgccatgtc aa 22

<210> SEQ ID NO 51
<211> LENGTH: 22
<212> TYPE: DNA
<213> ORGANISM: Papaver somniferum

<400> SEQUENCE: 51
gtttcgcaag ctcctgcata gt 22

<210> SEQ ID NO 52
<211> LENGTH: 37
<212> TYPE: DNA
<213> ORGANISM: Papaver somniferum

<400> SEQUENCE: 52
aaactcgaga agcttatgat catgagtaac ttatgga 37

<210> SEQ ID NO 53
<211> LENGTH: 28
<212> TYPE: DNA
<213> ORGANISM: Papaver somniferum

<400> SEQUENCE: 53
aaaggtaccc caacaggcca ttccgttg 28

-continued

```
<210> SEQ ID NO 54
<211> LENGTH: 33
<212> TYPE: DNA
<213> ORGANISM: Papaver somniferum

<400> SEQUENCE: 54

aaactcgaga agctttagga gggtatgtcc ggc                               33


<210> SEQ ID NO 55
<211> LENGTH: 28
<212> TYPE: DNA
<213> ORGANISM: Papaver somniferum

<400> SEQUENCE: 55

aaaggtacct taactccgcc tcggctcc                                     28


<210> SEQ ID NO 56
<211> LENGTH: 36
<212> TYPE: DNA
<213> ORGANISM: Artificial
<220> FEATURE:
<223> OTHER INFORMATION: oligo T primer for cDNA synthesis

<400> SEQUENCE: 56

attctagatc cracatgttt tttttttttt tttttt                            36
```